(12) United States Patent
Tatsutani

(10) Patent No.: US 9,316,658 B2
(45) Date of Patent: Apr. 19, 2016

(54) SAMPLE PROCESSING APPARATUS THAT RESPONDS TO TROUBLE IN A TRANSPORT UNIT

(75) Inventor: Hiroo Tatsutani, Kobe (JP)

(73) Assignee: SYSMEX CORPORATION, Kobe-Shi (JP)

( * ) Notice: Subject to any disclaimer, the term of this patent is extended or adjusted under 35 U.S.C. 154(b) by 756 days.

(21) Appl. No.: 13/073,376

(22) Filed: Mar. 28, 2011

(65) Prior Publication Data

US 2011/0244582 A1  Oct. 6, 2011

(30) Foreign Application Priority Data

Mar. 30, 2010 (JP) ................ 2010-079195

(51) Int. Cl.
| | |
|---|---|
| G01N 35/04 | (2006.01) |
| G01N 35/02 | (2006.01) |
| G01N 35/00 | (2006.01) |
| G01N 1/28 | (2006.01) |

(52) U.S. Cl.
CPC .......... *G01N 35/04* (2013.01); *G01N 35/00584* (2013.01); *G01N 1/2813* (2013.01); *G01N 2035/00643* (2013.01); *G01N 2035/00752* (2013.01); *G01N 2035/00801* (2013.01); *G01N 2035/0462* (2013.01); *G01N 2035/0465* (2013.01); *G01N 2035/0467* (2013.01); *Y10T 436/113332* (2015.01)

(58) Field of Classification Search
CPC ........................................... G01N 2035/00643
See application file for complete search history.

(56) References Cited

U.S. PATENT DOCUMENTS 5,087,423 A * 2/1992 Ishibashi .................... 422/67
6,723,288 B2 * 4/2004 Devlin et al. ............... 422/65

FOREIGN PATENT DOCUMENTS

| CN | 101520464 A | 9/2009 |
|---|---|---|
| JP | 03-285175 A | 12/1991 |
| JP | 2002-318237 A | 10/2002 |
| JP | 2003-057251 A | 2/2003 |
| JP | 2003-121451 A | 4/2003 |

* cited by examiner

*Primary Examiner* — Yelena G Gakh
*Assistant Examiner* — Michelle Adams

(57) ABSTRACT

A sample processing apparatus comprising: a plurality of testing units arranged along a transport path and each configured to perform at least one type of test; a plurality of transport units configured to collectively constitute the transport path and collectively function to deliver samples to the plurality of testing units for testing; and at least one processor of a computer system and at least one memory that stores programs executable by the at least one processor to: (a) determine a type of test required to be performed on a sample; (b) if a trouble of a transport unit is reported, determine whether there is an available testing unit performable of the required type of test to which the sample is deliverable; (c) if there is the available testing unit, instruct to transport the sample to the available testing unit.

13 Claims, 20 Drawing Sheets

SAMPLE PROCESSING APPARATUS THAT RESPONDS TO TROUBLE IN A TRANSPORT UNIT

RELATED APPLICATIONS

This application claims priority under 35 U.S.C. §119 to Japanese Patent Application No. 2010-079195 filed on Mar. 30, 2010, the entire content of which is hereby incorporated by reference.

BACKGROUND OF THE INVENTION

1. Field of the Invention

The present invention relates to a sample processing apparatus, a sample transporting method, and a non-transitory storage medium for transporting a sample to a testing unit.

2. Description of the Related Art

In Japanese Laid-Open Patent Publication No. 2002-318237, there is a description of a sample rack transport system which includes a transport apparatus in which a plurality of line units are connected in series, a supply section supplying a sample rack to the transport apparatus, and a controller for storing information relating to a processing status of the sample rack and controlling the transport apparatus. In this sample rack transport system, a transport line for transporting a sample rack and a return line for returning a sample rack to the upstream side of the transport line are configured by connecting the plurality of line units and sample racks can be transported to sample processing units corresponding to the respective line units via the transport line.

If trouble occurs during the transport of a sample rack in this sample rack transport system, after the system is restored from the trouble, the controller performs controls the transport apparatus so as to supply a sample rack to a sample processing unit which is to be the next transport destination on the basis information relating to the rack processing status.

However, in the above-described sample rack transport system, when trouble occurs during the transport of a sample rack, the transport operation of the sample rack by the sample rack transport system is completely stopped until the trouble is resolved.

SUMMARY OF THE INVENTION

The scope of the present invention is defined solely by the appended claims, and is not affected to any degree by the statements within this summary.

According to a first aspect of the present invention, a sample processing apparatus comprising:

a plurality of testing units arranged along a transport path and each configured to perform at least one type of test;

a plurality of transport units configured to collectively constitute the transport path and collectively function to deliver samples to the plurality of testing units for testing; and at least one processor of a computer system and at least one memory that stores programs executable by the at least one processor to:

(a) determine a type of test required to be performed on a sample;

(b) if a trouble of a transport unit is reported, determine whether there is an available testing unit performable of the required type of test to which the sample is deliverable;

(c) if there is the available testing unit, instruct to transport the sample to the available testing unit.

According to a second aspect of the present invention, a sample transporting method executed in a sample processing apparatus comprising a plurality of testing units arranged along a transport path and each configured to perform at least one type of test and a plurality of transport units configured to collectively constitute the transport path and collectively function to deliver samples to the plurality of testing units for testing, the method comprising computer-executable steps executed by at least one processor of a computer system to implement:

(a) determining a type of test required to be performed on a sample;

(b) if a trouble of a transport unit is reported, determining whether there is an available testing unit performable of the required type of test to which the sample is deliverable;

(c) if there is the available testing unit, instructing to transport the sample to the available testing unit.

According to a third aspect of the present invention, a non-transitory storage medium provided in a sample processing apparatus which comprises a plurality of testing units arranged along a transport path and each configured to perform at least one type of test and a plurality of transport units configured to collectively constitute the transport path and collectively function to deliver samples to the plurality of testing units for testing, the storage medium storing programs executed by at least one processor of a computer system to:

(a) determine a type of test required to be performed on a sample;

(b) if a trouble of a transport unit is reported, determine whether there is an available testing unit performable of the required type of test to which the sample is deliverable;

(c) if there is the available testing unit, instruct to transport the sample to the available testing unit.

DETAILED DESCRIPTION OF THE PREFERRED EMBODIMENTS

Hereinafter, preferred embodiments of the invention will be described with reference to the drawings.

(First Embodiment)

This embodiment is a sample rack transport system which includes an insertion apparatus for inserting sample racks containing a plurality of samples, a sample transport apparatus transporting an inserted sample rack and supplying the sample rack to a measuring apparatus and a plurality of recovery apparatuses recovering sample racks to sort and recover sample racks into the plurality of recovery apparatuses in accordance with whether all the measurement items based on a measurement order are measured when trouble (abnormality) occurs. Here, in this embodiment, the trouble is not a small problem such as a mistake in the transport of sample racks, but is a severe problem which requires repair by a service man due to a physical breakdown of the transport mechanism of the sample transport apparatus.

Figure 1:
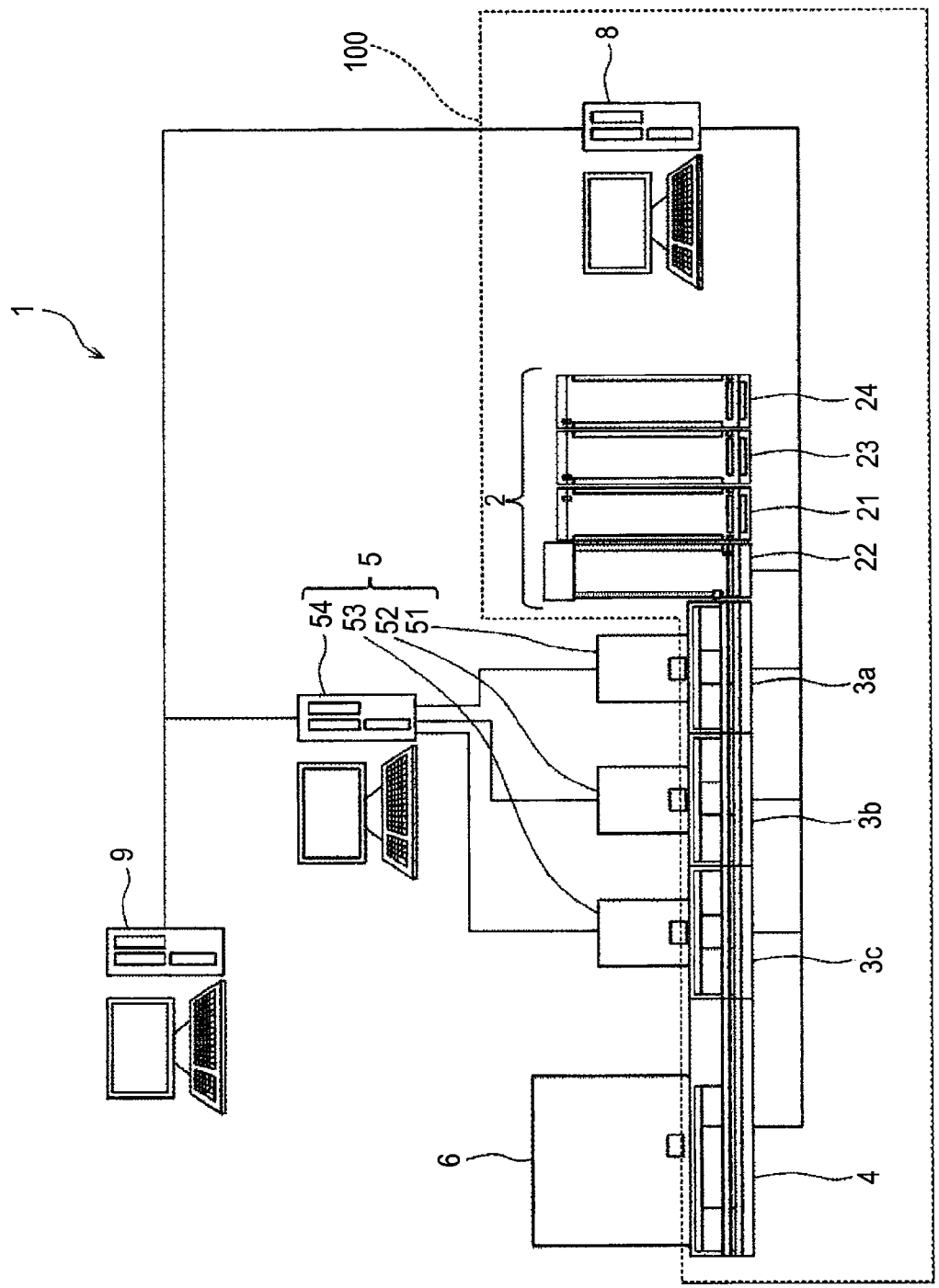
FIG. 1 is a schematic plan view showing the overall configuration of a sample processing apparatus according to a first embodiment.

FIG. 1 is a schematic plan view showing the overall configuration of a sample processing system 1 including the sample rack transport system according to this embodiment. As shown in FIG. 1, the sample rack transport system 100 includes a sample insertion and recovery apparatus 2, sample transport apparatuses 3a, 3b, 3c and 4 and a system control apparatus 8. In addition, the sample processing system 1 includes a sample rack transport system 100, a blood cell analysis apparatus 5 and a smear preparation apparatus 6. In addition, the sample processing system 1 according to this embodiment is connected to an examination information management apparatus 9 so as to communicate therewith via a communication network.

<Configuration of Sample Insertion and Recovery Apparatus 2>

Figure 2:
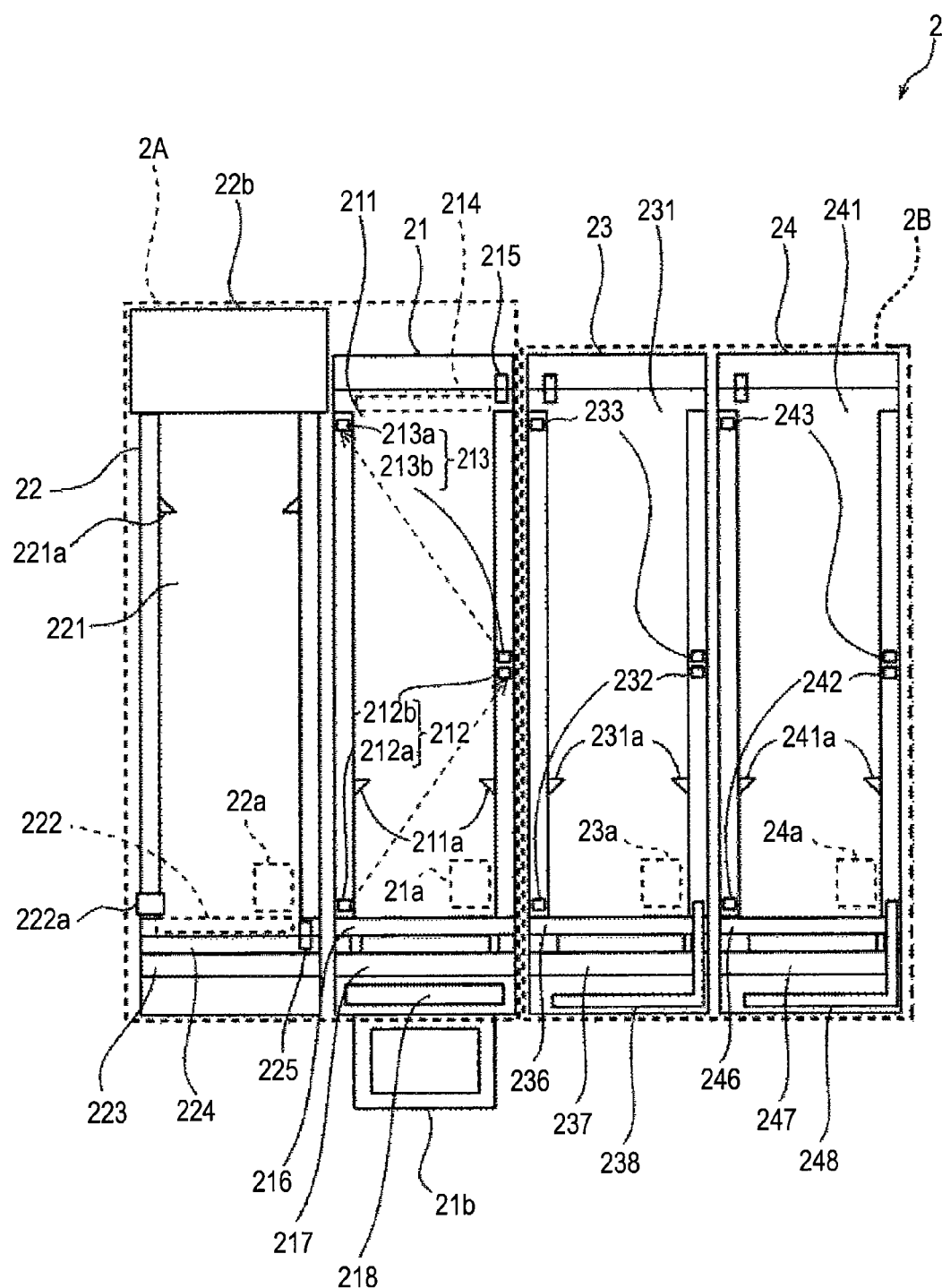
FIG. 2 is a plan view showing the configuration of a sample insertion and recovery apparatus according to the first embodiment.

FIG. 2 is a plan view showing the configuration of the sample insertion and recovery apparatus 2 according to this embodiment. The sample insertion and recovery apparatus 2 includes a sample insertion unit 21, a pre-processing unit 22 and sample recovery units (rack recovery section) 23 and 24. In the sample insertion and recovery apparatus 2, sample racks can be placed which accommodate a plurality of sample containers. Such a sample insertion and recovery apparatus 2 has a sample insertion unit group 2A including the sample insertion unit 21 and the pre-processing unit 22 and a sample recovery unit group 2B including the sample recovery units 23 and 24.

Figure 3:
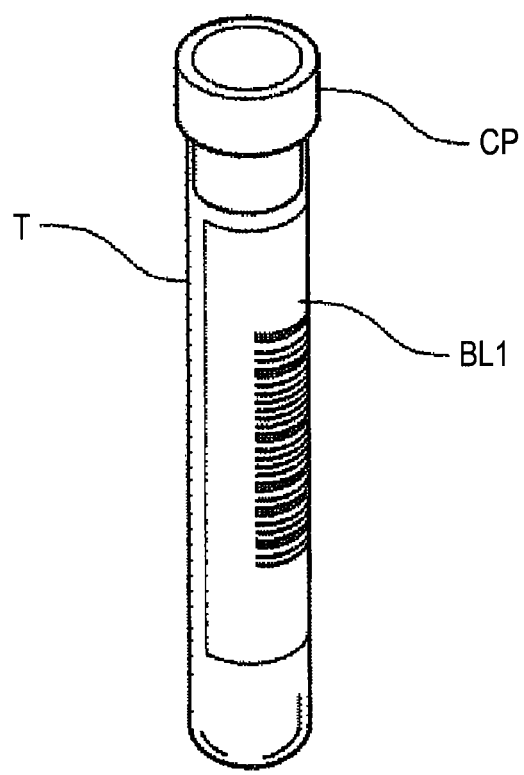
FIG. 3 is a perspective view showing the appearance of a sample container.
Figure 4:
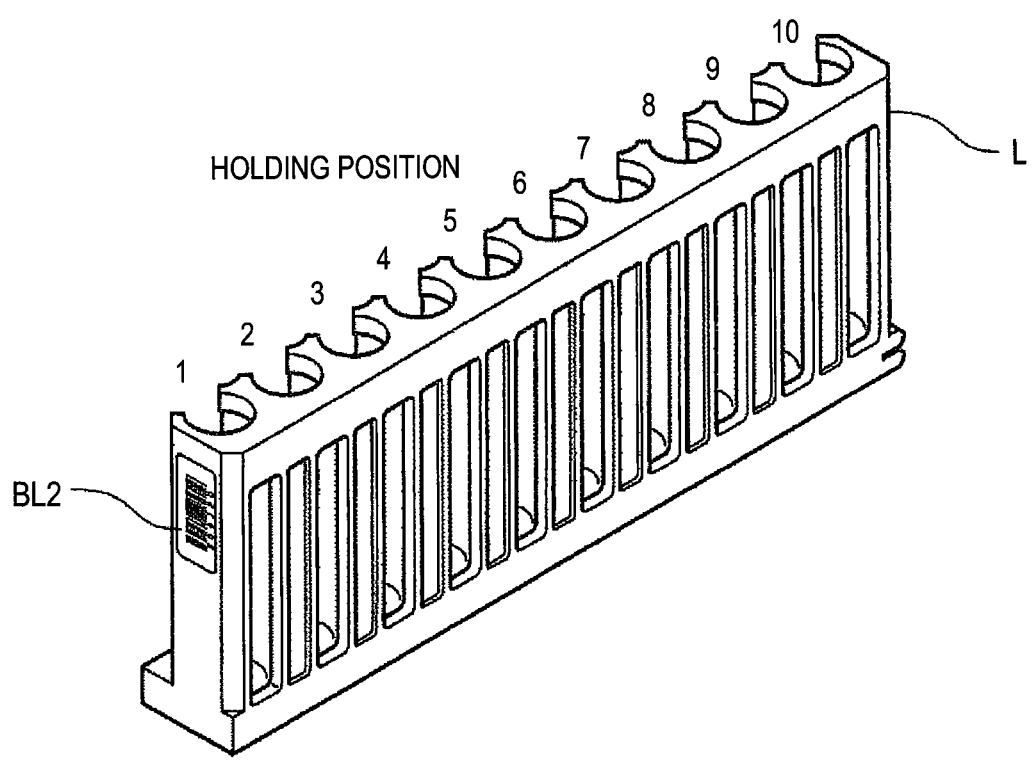
FIG. 4 is a perspective view showing the appearance of a sample rack.

FIG. 3 is a perspective view showing the appearance of a sample container T and FIG. 4 is a perspective view showing the appearance of a sample rack L. As shown in FIG. 3, the sample container T has a tubular shape and the upper end thereof is opened. A blood sample collected from a patient is contained in the sample container and the opening at the upper end is sealed by a cap section CP. The sample container T is made of glass or a synthetic resin having translucency and the blood sample therein can be visually confirmed. In addition, a barcode label BL1 is adhered to the side surface of the sample container T. A barcode (sample barcode) showing a sample ID is printed on this barcode label BL1. In the sample rack L, 10 sample containers T can be arranged in parallel and held. In the sample rack L, sample containers T are held in a vertical state (erect state). In addition, a barcode label BL2 is adhered to the side surface of the sample rack L. A barcode (rack barcode) showing a rack ID is printed on this barcode label BL2.

As shown in FIG. 2, the sample insertion unit 21 has a concave-shaped rack placement section 211 for placing a sample rack L accommodating sample containers T. This rack placement section 211 has a rectangular shape and a plurality of sample racks L can be placed at the same time therein. Sample racks L are placed in the rack placement section 211 so that sample containers T are arranged in parallel in the transverse direction. The rack placement section 211 is provided with sensors 212 and 213 for detecting a sample rack L and engagement sections 211a for transferring a sample rack L. The sensors 212 and 213 are optical sensors. The sensor 212 includes a light-emitting section 212a and a light-receiving section 212b, and the sensor 213 includes a light-emitting section 213a and a light-receiving section 213b. The light-emitting section 212a is disposed on the front-left side of the rack placement section 211 and the light-receiving section 212b is disposed on the central-right side of the rack placement section 211. In addition, the light-emitting section 213a is disposed on the rear-left side of the rack placement section 211 and the light-receiving section 213b is disposed on the central-right side of the rack placement section 211. The light-emitting section 212a is disposed so as to emit light in the diagonally backward right direction and the light-receiving section 212b is disposed so as to receive this light across the rack placement section 211. The light-emitting section 213a is disposed so as to emit light in the diagonally forward right direction and the light-receiving section 213b is disposed so as to emit this light across the rack placement section 211. Accordingly, the light emitted from the light-emitting section 212a or 213a is shielded by a sample rack L placed in the rack placement section 211 and the sample rack L is detected by the rack sensor 212 or 213 due to a lowering of the light-reception level of the light-receiving section 212b or 213b. The sample rack L detected by the rack sensor 212 or 213 engages with the engagement sections 211a and moves forward and backward while the engagement sections 211a engage with the sample rack L. Therefore, the sample rack L is transferred on the rack placement section 211.

The position on the innermost side of the rack placement section 211 serves as a rack output position 214 for outputting a sample rack L to the left side. Such a rack output position 214 is provided with a protrusion section 215 which is movable left- and rightward. This protrusion section 215 waits at the position near the right end of the rack output position 214 until a sample rack L is transferred to the rack output position 214. When the sample rack L reaches the rack output position 214, the protrusion section moves leftward. The sample rack L is pushed by the protrusion section 215 and moves leftward. In addition, the walls on the both right and left sides of the rack output position 214 are missing. Accordingly, the sample rack L pushed by the protrusion section 215 is output from the sample insertion unit 21. As shown in FIG. 2, the pre-processing unit 22 is provided on the left side of the sample insertion unit 21 and the wall on the right side of the pre-processing unit 22 is partially missed, so the sample rack L output from the rack output position 214 is introduced into the pre-processing unit 22.

In addition, two parallel belt conveyors, that is, a first transport line 216 and a second transport line 217 are provided in front of the rack placement section 211. Portions on both right and left sides of the first transport line 216 and the second transport line 217 of the wall surrounding the rack placement section 211 of the sample insertion unit 21 are missed to introduce sample racks L into the first transport line 216 and the second transport line 217 and to discharge sample racks L to another unit from the first transport line 216 and the second transport line 217. The bottom surface of the rack placement section 211 and the heights of the first transport line 216 and the second transport line 217 are uniformized and almost the uniform plane is formed. In addition, the sample insertion unit 21 is provided with a rack transfer section 218 for transferring a sample rack L introduced into the first transport line 216 or the second transport line 217 in the backward direction. Such a rack transfer section 218 has a horizontally long rod shape and is movable forward and backward in the range from the second transport line 217 to the central position in the front-back direction of the rack placement section 211. Due to the backward movement of the rack transfer section 218 which is displaced in front of a sample rack L introduced into the first transport line 216 or the second transport line 217, the rack transfer section 218 is brought into contact with the front surface of the sample rack L, and due to further backward movement of the rack transfer section 218, the sample rack L is pushed and moved backward. Accordingly, the sample rack L is transferred backward up to a position past the engagement sections 211a and then the sample rack L is transferred up to the rack output position 214 by the engagement sections 211a. In this manner, the sample insertion unit 21 can directly output a sample rack L which is introduced by the first transport line 216 or the second transport line 217 to the sample recovery unit 23 on the right side, and can transfer a sample rack L on the first transport line 216 or the second transport line 217 up to the rack output position 214 and then output the sample rack to the pre-processing unit 22 on the left side.

The sample insertion unit 21 having such a configuration includes a control section 21a including a CPU, a memory and the like. The above-described mechanisms in the sample insertion unit 21 are controlled by this control section 21a. In addition, the sample insertion unit 21 includes an Ethernet (registered trade name) interface and is connected to an information processing unit 54 and the system control apparatus 8 via a LAN so as to communicate therewith. The sample insertion unit 21 is provided with an operation panel 21b. A user can give an instruction for starting or ending sample processing to the sample processing system 1 by operating the operation panel 21b.

The pre-processing system 22 is connected to the left side of the sample insertion unit 21. A sample rack L output to the left side from the rack output position 214 is introduced into the pre-processing unit 22. Such a pre-processing unit 22 includes a rack placement section 221, which can accommodate a plurality of sample racks L and has a quadrangular shape in a planar view. In addition, the pre-processing unit 22 includes a barcode reading section 22b on the inside of the rack placement section 221. Such a barcode reading section 22b can read sample barcodes of a plurality of sample containers T accommodated in a sample rack L at the same time and can also read a rack barcode of the sample rack L. Such a barcode reading section 22b is provided with an optical sensor (not shown) for detecting a sample container T. When a sample rack L reaches a position at which the barcode reading section 22b reads a barcode, whether there is a sample container T is detected by the optical sensor. In addition, the barcode reading section 22b includes a horizontal rotating mechanism (not shown) which horizontally rotates a plurality of sample containers T immediately above the barcode reading position on the innermost side of the rack placement section 221. A sample rack L output from the rack output position 214 of the rack insertion unit 21 is introduced leftward into the pre-processing unit 22 and reaches the barcode reading position. Then, while the horizontal rotating mechanism horizontally rotates a sample container T accommodated in the sample rack L, the barcode reading section 22b reads out a sample ID from a barcode label BL1 and reads out a rack ID from a barcode label BL2 of the sample rack L.

When the sample rack L reaches the barcode reading position, whether there is a sample container T is detected by the above-described optical sensor and the barcode reading section 22b continuously reads a sample barcode of each of the sample containers T plural times. When data of the sample IDs, each of which is read plural times matches, the reading of the sample barcode is regarded as successful and the sample IDs and the read rack ID are transmitted to the system control apparatus 8.

Engagement sections 221a protrude from both right and left walls of the rack placement section 221. Such engagement sections 221a engage with a sample rack L of which a rack barcode and sample barcodes have been read by the barcode reading section 22b and moves forward. Accordingly, the sample rack L moves forward on the rack placement section 221. The position on the foremost side of the rack placement section 221 serves as a rack output position 222. A transport line 223 which is a belt conveyor is provided in front of this rack output position 222 and a partition section 224 having a wall shape protrudes between the transport line 223 and the rack output position 222. The partition section 224 is provided with a protrusion section 225 which is movable left- and rightward. This protrusion section 225 waits at the position near the right end of the rack output position 222 until a sample rack L is transferred to the rack output position 222. After the sample rack L reaches the rack output position 222, the protrusion section moves leftward. The sample rack L is pushed by the protrusion section 225 and moves leftward. In addition, the walls on the both right and left sides of the rack output position 222 are missing. Accordingly, the sample rack L pushed by the protrusion section 225 is output from the pre-processing unit 22. As shown in FIG. 1, the sample transport apparatus 3a is connected to the left side of the pre-processing unit 22 and the rack output position 222 linearly connects with an overtaking line to be described later of the sample transport apparatus 3a. Accordingly, the sample rack L output from the rack output position 222 is introduced into the overtaking line of the sample transport apparatus 3a.

In addition, a barcode reader 222a for reading a rack barcode is provided near the rack output position 222. This barcode reader 222a reads the rack ID of a sample rack L transported to the rack output position 222 and the read rack ID is transmitted to the system control apparatus 8. As will be described later, the system control apparatus 8 receives this rack ID and decides a transport destination of the sample rack L in accordance with the rack ID.

In addition, walls on both right and left sides of the transport line 223 are missed and the transport line 223 linearly connects with a return line to be described later of the sample transport apparatus 3a and the above-described second transport line 217 of the sample insertion unit 21. Accordingly, the transport line 223 receives a sample rack L from the return line of the sample transport apparatus 3a and discharges this sample rack L to the second transport line 217 of the sample insertion unit 21.

The pre-processing unit 22 having such a configuration includes a control section 22a including a CPU, a memory and the like. The above-described mechanisms in the pre-processing unit 22 are controlled by this control section 22a. In addition, the pre-processing unit 22 includes an Ethernet (registered trade name) interface and is connected to the information processing unit 54 and the system control apparatus 8 via a LAN so as to communicate therewith.

On the right side of the sample insertion unit 21, sample recovery units 23 and 24 are laterally arranged side by side. The sample insertion unit 21 is connected to the leftmost sample recovery unit 23. These sample recovery units 23 and 24 have the same configuration as that of the rack insertion unit 21. That is, the sample recovery units 23 and 24 include concave-shaped rack placement sections 231 and 241 for placing sample racks L, engagement sections 231a and 241a for transferring sample racks L placed in the rack placement sections 231 and 241 backward, sensors 232 and 233 and 242 and 243 for detecting sample racks L, first transport lines 236 and 246 and second transport lines 237 and 247 which are provided in front of the rack placement sections 231 and 241 to transport sample racks L in the transverse direction, and rack transfer sections 238 and 248 for transferring sample racks L, which are introduced into the first transport lines 236 and 246 or the second transport lines 237 and 247, to the rack placement sections 231 and 241, respectively. The sample recovery units 23 and 24 are connected so that the first transport lines 236 and 246 linearly connect with each other and the second transport lines 237 and 247 linearly connect with each other.

The sample recovery units 23 and 24 include control sections 23a and 24a including a CPU, a memory and the like, respectively. The above-described mechanisms in the sample recovery units 23 and 24 are controlled by these control sections 23a and 24a. In addition, the respective sample recovery units 23 and 24 include an Ethernet (registered trade name) interface and are connected to the information processing unit 54 and the system control apparatus 8 via a LAN so as to communicate therewith.

The sample recovery unit 24 is used to recover a sample rack L in which the necessary measurement has been completed. In addition, the sample recovery unit 23 is used to recover a sample rack L in which the necessary measurement has not been completed due to the occurrence of trouble in the sample transport apparatus 3a, 3b or 3c.

<Configurations of Sample Transport Apparatuses 3a, 3b and 3c>

Next, the configurations of the sample transport apparatuses 3a, 3b and 3c will be described. As shown in FIG. 1, the sample rack transport system 100 includes the sample transport apparatuses 3a, 3b and 3c. The sample transport apparatuses 3a, 3b and 3c are disposed in front of three measuring units 51, 52 and 53 of the blood cell analysis apparatus 5, respectively. The neighboring sample transport apparatuses are connected to each other to deliver and receive a sample rack L. In addition, the rightmost sample transport apparatus 3a is connected to the above-described sample insertion and recovery apparatus 2 to introduce a sample rack L discharged from the sample insertion and recovery apparatus 2 and to output a sample rack L to the sample insertion and recovery apparatus 2.

Figure 5:
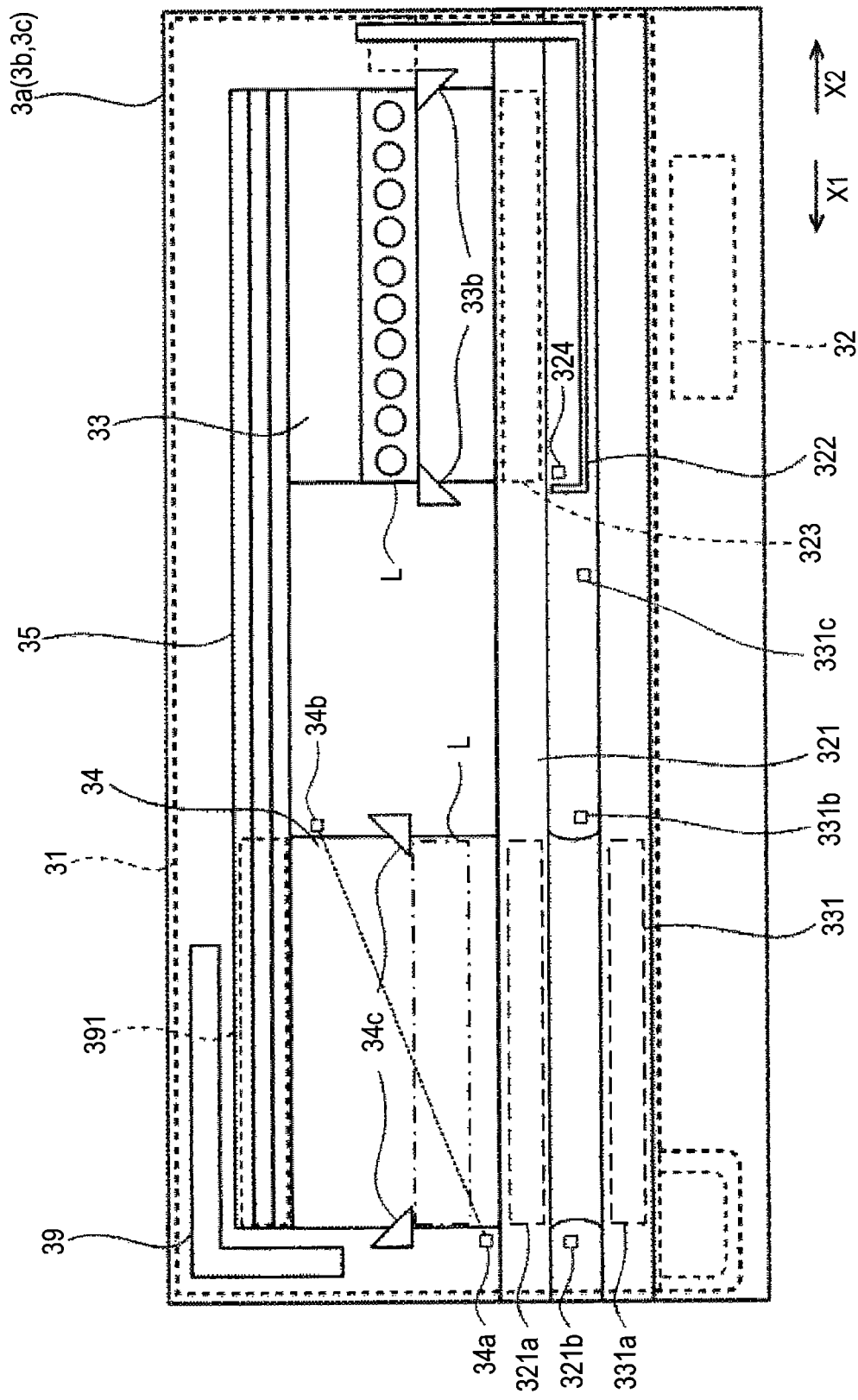
FIG. 5 is a plan view showing the configuration of a sample transport apparatus for a blood cell analysis apparatus according to the first embodiment.

FIG. 5 is a plan view showing the configurations of the sample transport apparatuses 3a, 3b and 3c. Here, the sample transport apparatus 3a which is disposed in front of the measuring unit 51 will be described, but the sample transport apparatuses 3b and 3c which are disposed in front of the measuring units 52 and 53, respectively, have the same configuration. As shown in FIG. 5, the sample transport apparatus 3a includes a transport mechanism 31 transporting a sample and a control section 32 controlling the transport mechanism 31.

The transport mechanism 31 includes a pre-analysis rack holding section 33 capable of temporarily holding a sample rack L which holds a sample container T containing a sample before analysis, a post-analysis rack holding section 34 capable of temporarily holding a sample rack L which holds a sample container T in which a sample has been suctioned by the corresponding measuring unit 51, a rack transport section 35 which horizontally and linearly moves a sample rack L in the direction of the arrow X in the drawing to supply the sample rack to the measuring unit 51 and transports the sample rack L received from the pre-analysis rack holding section 33 to the post-analysis rack holding section 34, a rack overtaking transport section 321 which introduces a sample rack L from the apparatus (any one of the sample insertion and recovery apparatus 2 and the sample transport apparatus 3a and 3b) further to the upstream side of the transport and discharges the sample rack L to the apparatus (any one of the sample transport apparatuses 3b and 3c and the sample transport apparatus 4) further to the downstream side of the transport without supply of a sample contained in this sample rack L to the measuring unit 51, and a rack return transport section 331 which introduces a sample rack L from the apparatus (any one of the sample transport apparatuses 3b and 3c and the sample transport apparatus 4) further to the downstream side of the transport and discharges the sample rack L to the apparatus (any one of the sample insertion and recovery apparatus 2 and the sample transport apparatus 3a and 3b) further to the upstream side of the transport without supply of a sample contained in this sample rack L to the measuring unit 51. Each of the rack overtaking transport section 321 and the rack return transport section 331 have a transport belt for transporting a rack and a stepping motor driving the transport belt. The rack overtaking transport section 321 transports a sample rack L by driving the transport belt with the stepping motor in the transport downstream direction. In addition, the rack return transport section 331 transports a sample rack L by driving the transport belt with the stepping motor in the transport upstream direction.

When a sample rack L in the post-analysis rack holding section 34 is detected by optical sensors 34a and 34b including a light-emitting section and a light-receiving section, rack feeding mechanisms 34c move while engaging with the rear ends of the sample rack L and thus the sample rack L is positioned at any one of a rack overtaking position 321a and a rack return position 331a. Sensors 321b and 331b are provided near the rack overtaking position 321a and the rack return position 331a, respectively, and can detect the fact that a sample rack L has been positioned at the above position.

The control section 32 includes a CPU, a ROM, a RAM and the like (not shown). A control program of the transport mechanism 31 which is stored in the ROM can be executed by the CPU. In addition, such a control section 32 includes an Ethernet (registered trade name) interface and is connected to the information processing unit 54 and the system control apparatus 8 via a LAN so as to communicate therewith.

The sample transport apparatus 3a transports a sample rack L, which is transported from the sample insertion and recovery apparatus 2, to a pre-analysis rack output position 323 by the rack overtaking transport section 321, transfers the sample rack to the pre-analysis rack holding section 33 by a rack output section 322, outputs this sample rack L to the rack transport section 35 from the pre-analysis rack holding section 33 by rack feeding sections 33b, and transports the sample rack by the rack transport section 35 to supply a sample to the corresponding measuring unit 51 (52, 53) of the blood cell analysis apparatus 5. A sensor 324 capable of detecting the fact that a sample rack L is positioned at the position 323 is provided near the pre-analysis rack output position 323. In addition, the sample rack L containing the sample in which the suction has been completed is transferred to a post-analysis rack output position 391 by the rack transport section 35 and is output to the post-analysis rack holding section 34 by a rack output section 39. The sample rack L held in the post-analysis rack holding section 34 is transferred to the rack overtaking transport section 321 and is discharged to the subsequent apparatus by the rack overtaking transport section 321 when the sample which is contained in this sample rack L is required to be measured by the measuring unit 52 or 53 on the transport direction downstream side or to be provided to the preparation of a smear by the smear preparation apparatus 6. When there is no need to perform the measurement by the measuring unit 52 or 53 on the transport direction downstream side and the preparation of a smear by the smear preparation apparatus 6 on all of the samples which are held in the sample rack L held in the post-analysis rack holding section 34, the sample rack L is transferred to the rack return transport section 331 and is discharged to the preceding apparatus (on the upstream side in the transport direction) by the rack return transport section 331. In addition, when the sample rack L containing a sample to be processed by the measuring unit 52 or 53 further to the downstream side of the transport or by the smear preparation apparatus 6 is received from the preceding apparatus, this sample rack L is transported in the direction of the arrow X1 by the rack overtaking transport section 321 and is directly discharged to the subsequent apparatus 3. When the sample rack L which is recovered by the sample insertion and recovery apparatus 2 is received from the subsequent apparatus, this sample rack L is transported in the direction of the arrow X2 by the rack return transport section 331 and is directly discharged to the preceding sample insertion and recovery apparatus 2 or sample transport apparatus 3.

In the transport mechanism 31, the rack feeding sections 33b, the rack transport section 35 and the rack output section 39 are controlled by the information processing unit 54 of the blood cell analysis apparatus 5. The other parts in the transport mechanism 31 are controlled by the control section 32.

<Configuration of Sample Transport Apparatus 4>

As shown in FIG. 1, the sample transport apparatus 4 is disposed in front of the smear preparation apparatus 6. This sample transport apparatus 4 is connected to the sample transport apparatus 3c at the right end thereof.

Figure 6:
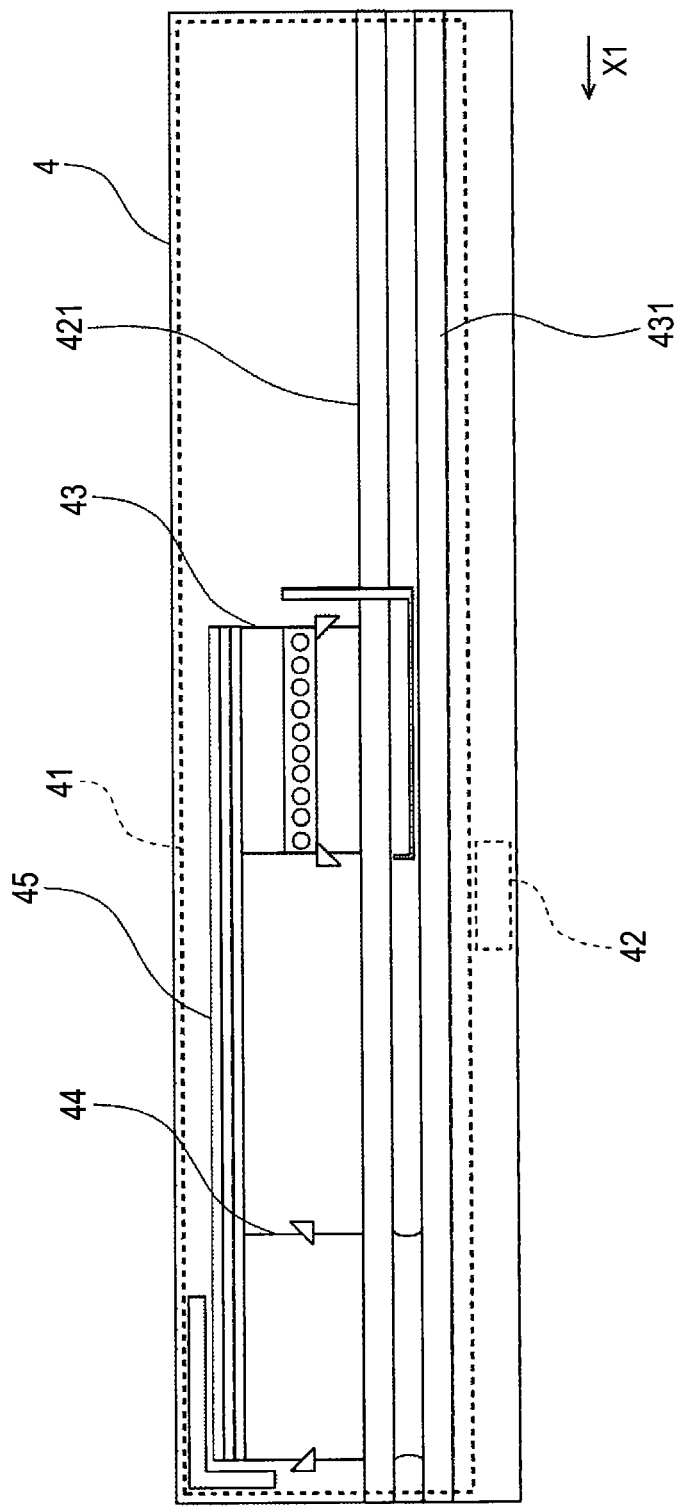
FIG. 6 is a plan view showing the configuration of a sample transport apparatus for a smear preparation apparatus according to the first embodiment.

FIG. 6 is a plan view showing the configuration of the sample transport apparatus 4. The sample transport apparatus 4 includes a transport mechanism 41 transporting a sample and a control section 42 controlling the transport mechanism 41. The transport mechanism 41 includes a pre-processing rack holding section 43 capable of temporarily holding a sample rack L which holds a sample container T containing a sample before preparation of a smear, a post-processing rack holding section 44 capable of temporarily holding a sample rack L which holds a sample container T in which a sample has been suctioned by the smear preparation apparatus 6, a rack transport section 45 which horizontally and linearly moves a sample rack L in the X1 direction to supply the sample to the smear preparation apparatus 6 and transports the sample rack L received from the pre-processing rack holding section 43 to the post-processing rack holding section 44, a rack overtaking transport section 421 which introduces a sample rack L from the sample transport apparatus 3c further to the upstream side of the transport and transports the sample rack L in the X1 direction, and a rack return transport section 431 which discharges a sample rack L to the sample transport apparatus 3c further to the upstream side of the transport in order to recover the sample rack L in which the preparation of smears of samples has been completed by the sample insertion and recovery apparatus 2. The sample transport apparatus 4 is different from the sample transport apparatuses 3a, 3b and 3c in sizes, shapes and positions of the constituent components. However, since the functions are the same, the description of the configuration thereof will be omitted.

The sample transport apparatus 4 introduces a sample rack L, which is discharged from the sample transport apparatus 3c on the upstream side, by the rack overtaking transport section 421, transfers the sample rack to the pre-processing rack holding section 43 by a rack output section (not shown), outputs this sample rack L to the rack transport section 45 from the pre-processing rack holding section 43, and transport the sample rack by the rack transport section 45 to supply a sample to the smear preparation apparatus 6. In addition, the sample rack L containing the sample in which the suction has been completed is transported by the rack transport section 45 and is output to the post-processing rack holding section 44 by the rack output section (not shown). The sample rack L held in the post-processing rack holding section 44 is transferred to the rack return transport section 431 and is discharged to the preceding sample transport apparatus 3c (on the upstream side in the transport direction) by the rack return transport section 431.

<Configuration of Blood Cell Analysis Apparatus 5>

The blood cell analysis apparatus 5 is an optical flow cytometry type multiple blood cell analysis apparatus. This apparatus obtains side-scattered light intensity, fluorescence intensity and the like with respect to blood cells included in a blood sample, classifies blood cells included in the sample on the basis of the above obtained results, counts the number of blood cells for each kind, and creates and displays a scattergram in which the classified blood cells are colored in different colors for each kind. Such a blood cell analysis apparatus 5 includes the measuring units 51, 52 and 53 which measure a blood sample and the information processing unit 54 which processes measurement data output from the measuring units 51, 52 and 53 and displays a blood sample analysis result.

As shown in FIG. 1, the blood cell analysis apparatus 5 includes the three measuring units 51, 52 and 53 and the single information processing unit 54. The information processing unit 54 is connected to the three measuring units 51, 52 and 53 so as to communicate therewith and can control the operations of the three measuring units 51, 52 and 53. In addition, the information processing unit 54 is connected to the three sample transport apparatuses 3a, 3b and 3c which are disposed in front of the three measuring units 51, 52 and 53, respectively, so as to communicate therewith.

Figure 7:
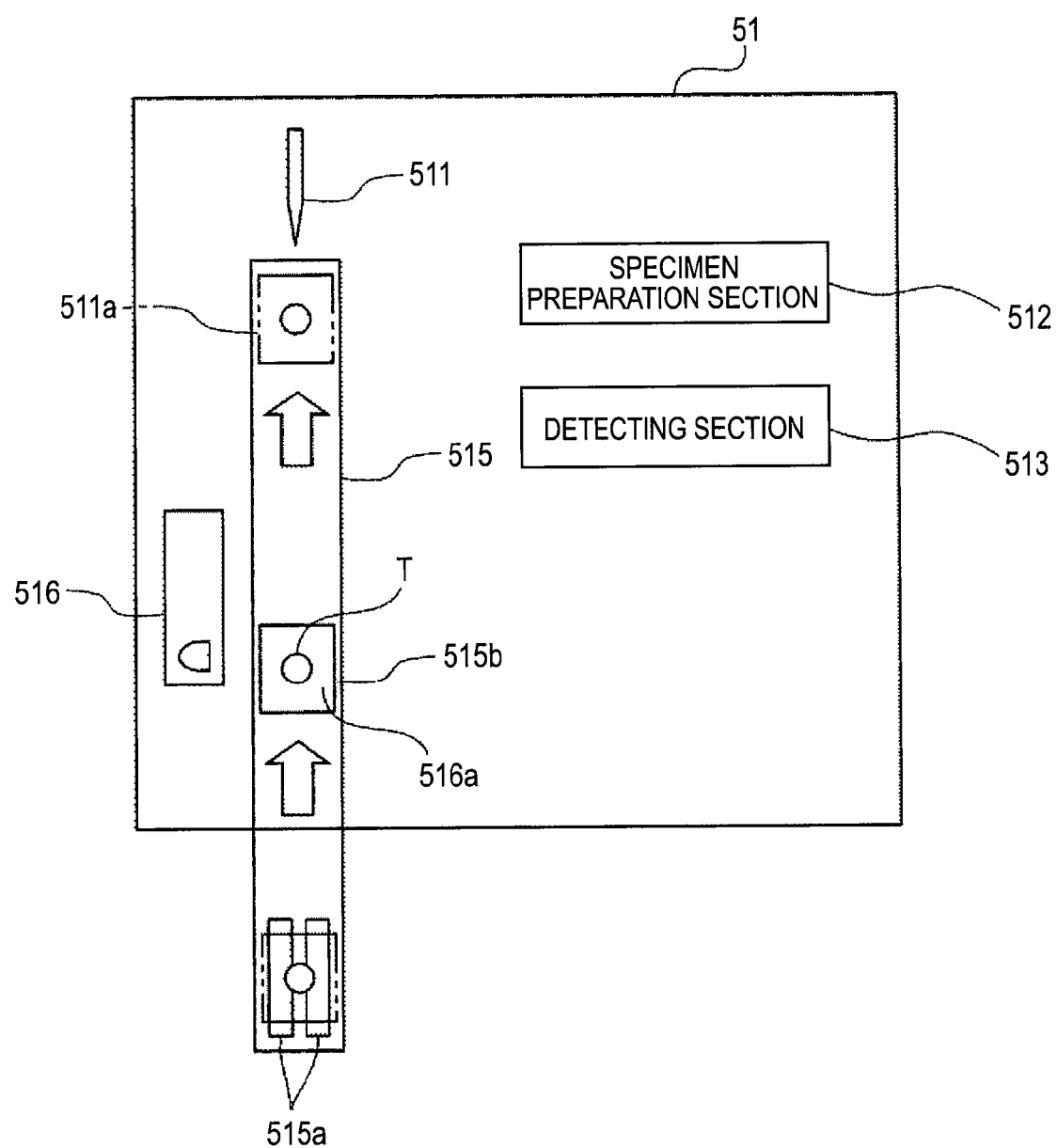
FIG. 7 is a block diagram showing the configuration of a measuring unit of the blood cell analysis apparatus according to the first embodiment.

FIG. 7 is a block diagram showing the configuration of the measuring unit 51. As shown in FIG. 7, the measuring unit 51 has a sample suction section 511 suctioning blood which is a sample from the sample container (blood collection tube) T, a specimen preparation section 512 preparing a measurement specimen which is used in measurement from the blood suctioned by the sample suction section 511 and a detecting section 513 detecting blood cells from the measurement specimen prepared by the specimen preparation section 512. In addition, the measuring unit 51 further has an intake port (not shown) for taking a sample container T which is accommodated in a sample rack L transported by the rack transport section 35 of the sample transport apparatus 3a into the measuring unit 51 and a sample container transport section 515 which takes a sample container T from a sample rack L into the measuring unit 51 and transports the sample container T up to a position at which the sample suction section 511 performs suction.

A suction tube (not shown) is provided at the tip end of the sample suction section 511. In addition, the sample suction section 511 is vertically movable and is configured to move downward so that the suction tube penetrates a cap section CP of a sample container T transported up to the suction position and suctions blood in the sample container.

The specimen preparation section 512 includes a plurality of reaction chambers (not shown). In addition, the specimen preparation section 512 is connected to reagent containers (not shown) and can supply reagents such as a dyeing reagent, a hemolytic agent and a diluent solution to the reaction chambers. The specimen preparation section 512 is also connected to the suction tube of the sample suction section 511 and can supply a blood sample suctioned by the suction tube to the reaction chambers. Such a specimen preparation section 512 mixes and stirs a sample and a reagent in the reaction chamber and prepares a specimen (measurement specimen) for the measurement by the detecting section 513.

The detecting section 513 can perform RBC (red blood cells) detection and PLT (platelets) detection by a sheath flow DC detection method. In the RBC and PLT detection by this sheath flow DC detection method, a measurement specimen in which a sample and a diluent solution are mixed is measured and measurement data obtained by the measurement is analyzed and processed by the information processing unit 54, and thus the RBC and PLT measurement is performed. In addition, the detecting section 513 can perform HGB (hemoglobin) detection by a SLS-hemoglobin method and is configured to perform WBC (white blood cells) detection by a flow cytometry method using a semiconductor laser. In this detecting section 513, a measurement specimen in which a sample, a hemolytic agent and a diluent solution are mixed is measured and measurement data obtained by the measurement is analyzed and processed by the information processing unit 54, and thus the WBC measurement is performed. The RBC, PLT, HGB and WBC are measured when a measurement item complete blood count (CBC) is designated.

The sample container transport section 515 includes a hand section 515a capable of gripping a sample container T. The hand section 515a includes a pair of gripping members which are disposed to be opposed to each other, and can move the gripping members closer to each other and separate the gripping members from each other. When such gripping members are moved closer to each other while gripping a sample container T, the sample container T can be gripped. In addition, the sample container transport section 515 can move the hand section 515a in the vertical direction and in the forward and backward directions (Y direction) and can oscillate the hand section 515a. Accordingly, when a sample container T which is accommodated in a sample rack L and is positioned at a sample supply position is gripped by the hand section 515a, and in this state, when the hand section 515a is moved upward to remove the sample container T from the sample rack L and is oscillated, the sample in the sample container T can be stirred.

In addition, the sample container transport section 515 includes a sample container setting section 515b having a hole into which a sample container T can be inserted. The sample container T gripped by the above-described hand section 515a is moved after completion of stirring and the gripped sample container T is inserted into the hole of the sample container setting section 515b. Then, by separating the gripping members from each other, the sample container T is set in the sample container setting section 515b. Such a sample container setting section 515b can horizontally move in the Y direction by a power of a stepping motor (not shown). In the measuring unit 51, a barcode reading section 516 is provided.

The sample container setting section 515b can move to a barcode reading position 516a near the barcode reading section 516 and to a position 511a at which the sample suction section 511 performs suction. When the sample container setting section 515b moves to the barcode reading position 516a, a set sample container T is horizontally rotated by the rotating mechanism (not shown) and a sample barcode is read by the barcode reading section 516. Accordingly, even when the barcode label BL1 of the sample container T is positioned on the opposite side to the barcode reading section 516, the barcode label BL1 can turn toward the barcode reading section 516 by rotating the sample container T and the sample barcode can be read by the barcode reading section 516. When the sample container setting section 515b moves to the suction position, the sample is suctioned from a set sample container T by the sample suction section 511.

The measuring units 52 and 53 have the same configuration as that of the measuring unit 51 and include a sample suction section, a specimen preparation section, a detecting section and a sample container transport section. However, the detecting section of the measuring unit 52 is different from the detecting section 513 of the measuring unit 51 and can perform a white blood cell-5-classification (measurement item DIFF) as well as CBC. In greater detail, the detecting section of the measuring unit 52 is configured to perform detection of WBC (white blood cells), NEUT (neutrophils), LYMPH (lymphocytes), EO (eosinophiles), BASO (basophils) and MONO (monocytes) by a flow cytometry method using a semiconductor laser. In such a detecting section of the measurement unit 52, a measurement specimen in which a dyeing reagent, a hemolytic agent and a diluent solution are mixed is measured and measurement data obtained by the measurement is analyzed and processed by the information processing unit 54, and thus the measurement of NEUT, LYMPH, EO, BASO, MONO and WBC is performed.

The detecting section of the measuring unit 53 is different from the detecting sections of the measuring units 51 and 52 and can measure reticulocytes (RET) in addition to CBC and DIFF. In order to perform the measurement of RET, a measurement specimen is prepared by mixing a reagent for RET measurement and a sample and the measurement specimen is supplied to an optical detecting section for WBC/DIFF (white blood cell-5-classification) detection of the detecting section.

Figure 8:
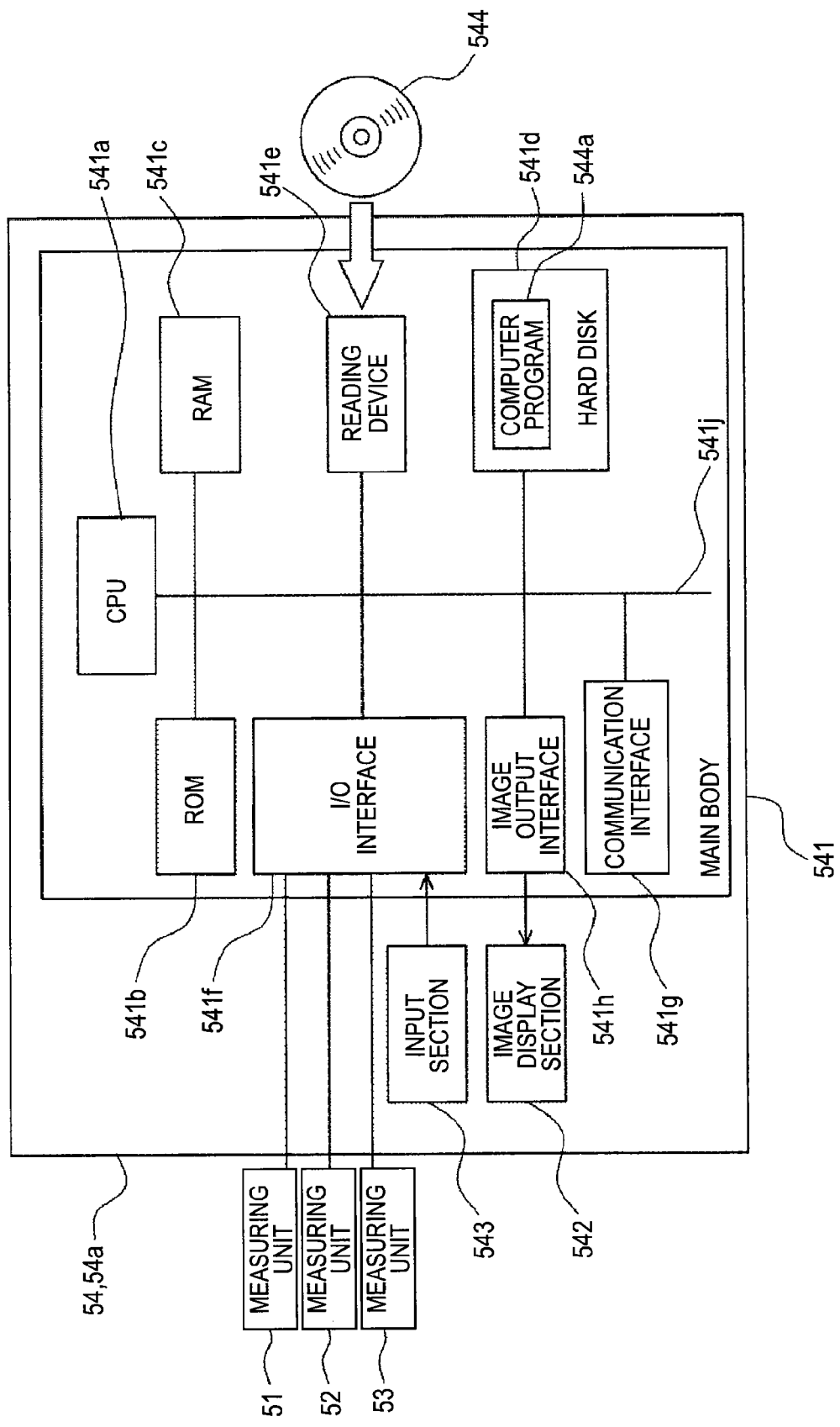
FIG. 8 is a block diagram showing the configuration of an information processing unit of the blood cell analysis apparatus according to the first embodiment.

Next, the configuration of the information processing unit 54 will be described. The information processing unit 54 is composed of a computer. FIG. 8 is a block diagram showing the configuration of the information processing unit 54. The information processing unit 54 is realized by a computer 54a. As shown in FIG. 8, the computer 54a includes a main body 541, an image display section 542 and an input section 543. The main body 541 includes a CPU 541a, a ROM 541b, a RAM 541c, a hard disk 541d, a reading device 541e, an I/O interface 541f, a communication interface 541g and an image output interface 541h. The CPU 541a, the ROM 541b, the RAM 541c, the hard disk 541d, the reading device 541e, the I/O interface 541f, the communication interface 541g and the image output interface 541h are connected to each other by a bus 541j.

The reading device 541e reads out a computer program 544a for prompting the computer to function as the information processing unit 54 from a portable recording medium 544 and can install the computer program 544a on the hard disk 541d.

<Configuration of Smear Preparation Apparatus 6>

The smear preparation apparatus 6 suctions a blood sample from a sample container T in a sample rack L, drops the sample onto a glass slide, thinly extends the blood sample on the glass slide and dries the sample. Then, the smear preparation apparatus supplies a dyeing solution to the glass slide to dye the blood on the glass slide, thereby preparing a smear.

<Configuration of System Control Apparatus 8>

The system control apparatus 8 is composed of a computer and controls the entire sample processing system 1. This system control apparatus 8 receives the number of a sample rack L from the sample insertion and recovery apparatus 2 and decides the transport destination of the sample rack L. In addition, the system control apparatus 8 monitors operation states of the respective apparatuses in the sample processing system 1, and when trouble occurs in the respective apparatuses, the system control apparatus can immediately detect the trouble.

Figure 9:
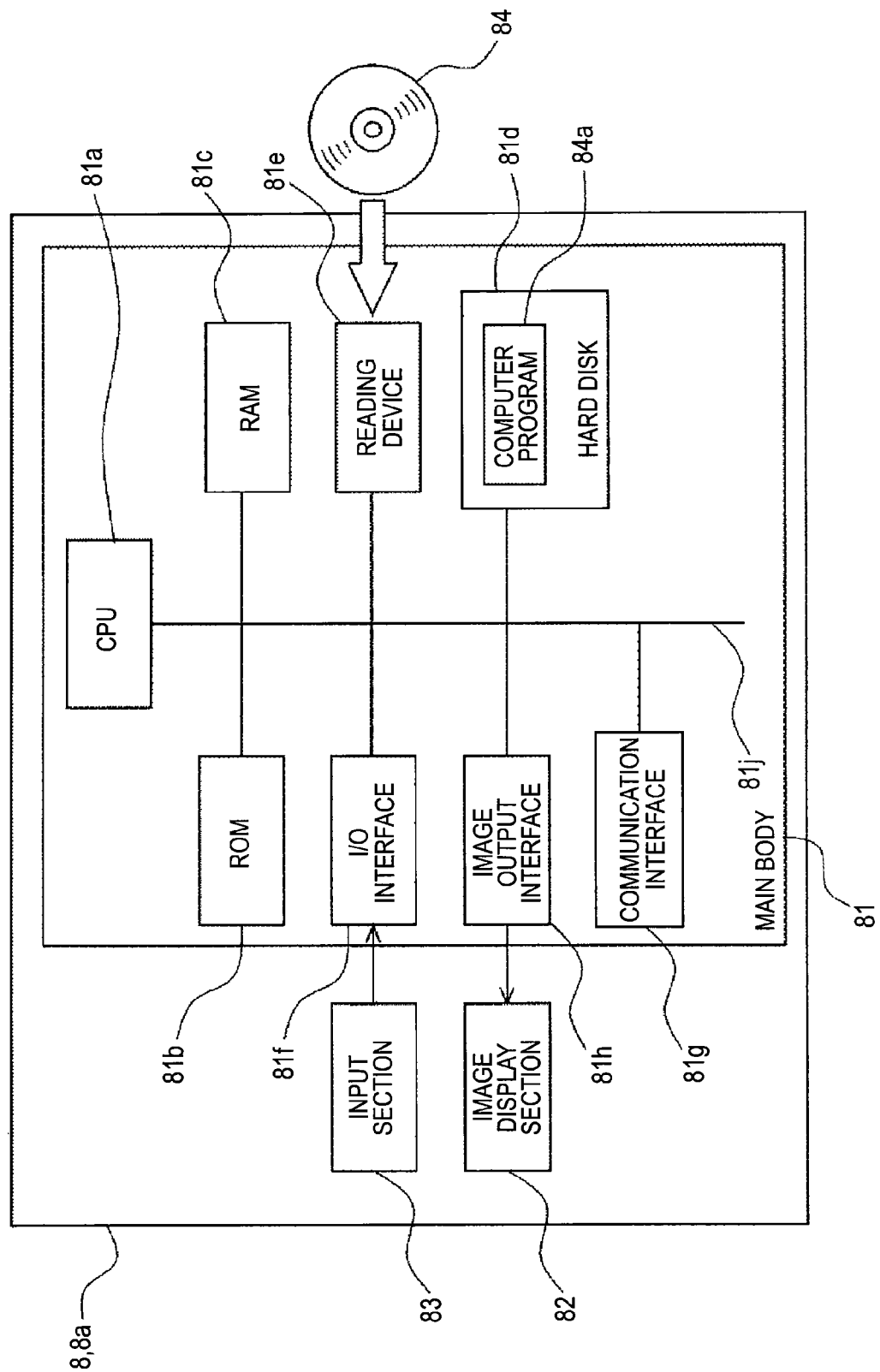
FIG. 9 is a block diagram showing the configuration of a system control apparatus according to the first embodiment.

FIG. 9 is a block diagram showing the configuration of the system control apparatus 8 according to this embodiment. The system control apparatus 8 is realized by a computer 8a. As shown in FIG. 9, the computer 8a includes a main body 81, an image display section 82 and an input section 83. The main body 81 includes a CPU 81a, a ROM 81b, a RAM 81c, a hard disk 81d, a reading device 81e, an I/O interface 81f, a communication interface 81g and an image output interface 81h. The CPU 81a, the ROM 81b, the RAM 81c, the hard disk 81d, the reading device 81e, the I/O interface 81f, the communication interface 81g and the image output interface 81h are connected to each other by a bus 81j.

The reading device 81e reads out a system control program 84a for prompting the computer to function as the system control apparatus 8 from a portable recording medium 84 and can install the system control program 84a on the hard disk 81d.

<Configuration of Examination Information Management Apparatus 9>

The examination information management apparatus 9 is an apparatus which manages information relating to examinations in facilities, that is, a so-called laboratory information system (LIS), and is connected not only to the blood cell analysis apparatus 5, but also to another clinical sample examination apparatus. Such an examination information management apparatus 9 receives a measurement order, which is input from an operator or is transmitted from another apparatus such as an electronic health record system, and stores and manages the measurement order. Further, the examination information management apparatus 9 receives an order request from the system control apparatus 8, transmits the requested measurement order to the system control apparatus 8, receives an analysis result from the blood cell analysis apparatus 5, and stores and manages this analysis result.

The examination information management apparatus 9 is composed of a computer and includes a CPU, a ROM, a RAM, a hard disk, a communication interface and the like. The communication interface is connected to the above-described LAN and can communicate with the system control apparatus 8 and the information processing unit 54 of the blood cell analysis apparatus 5. In addition, measurement orders are stored in the hard disk. In the measurement order, a sample ID and information regarding measurement items of an execution target are included. When receiving request data of a measurement order including a sample ID from another apparatus, the examination information management apparatus 9 reads out measurement data corresponding to this sample ID from the hard disk and transmits the measurement data to the apparatus which is the request source. Since the configuration of the examination information management apparatus 9 is the same as the configurations of the above-described other computers, the description thereof will be omitted.

[Operation of Sample Processing System]

Hereinafter, the operation of the sample processing system 1 according to this embodiment will be described.

<Sample Discharge Operation of Sample Insertion and Recovery Apparatus 2>

Figure 10:
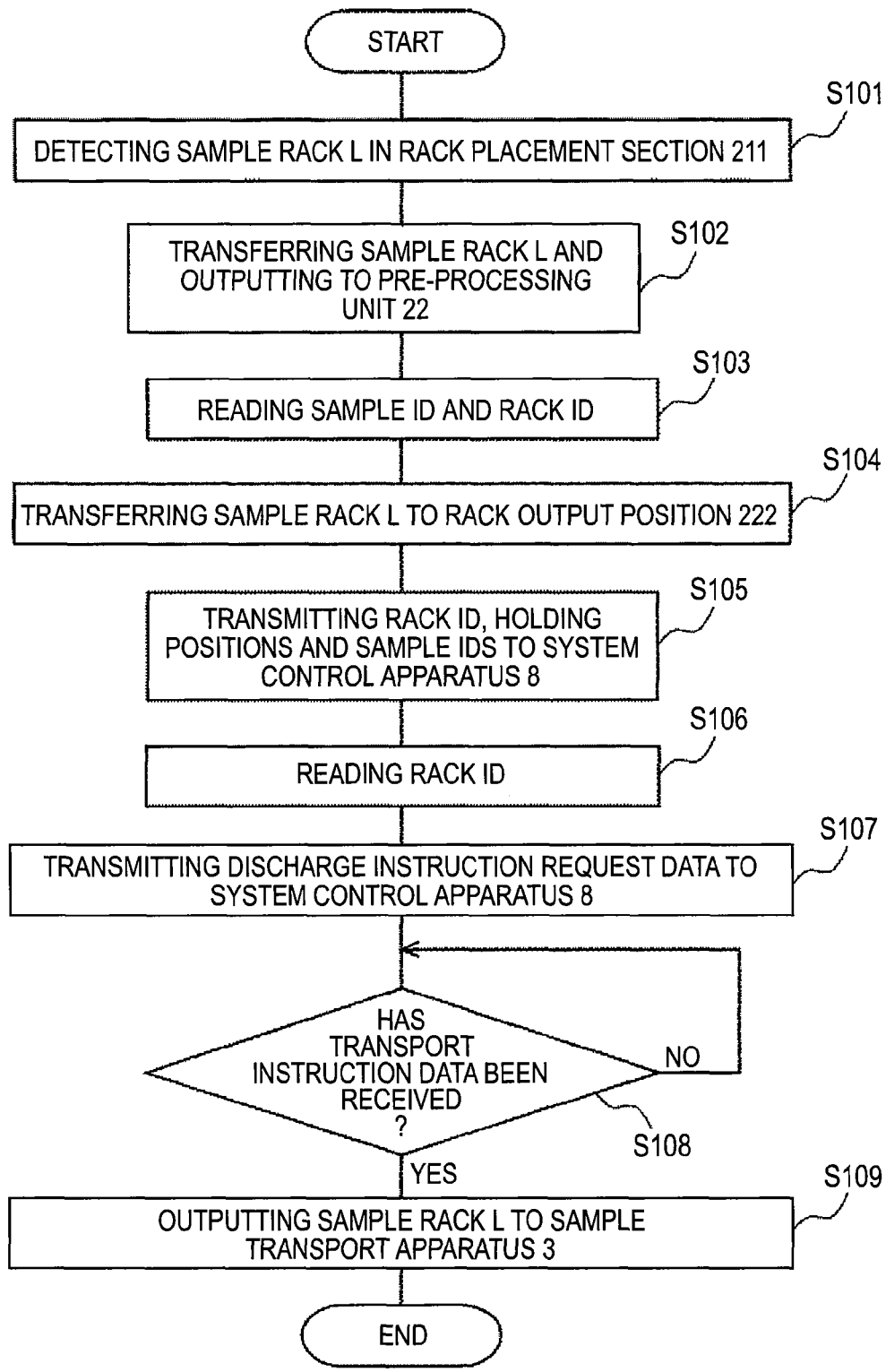
FIG. 10 is a flowchart showing the flow of a sample discharge operation of the sample insertion and recovery apparatus according to the first embodiment.

FIG. 10 is a flowchart showing the flow of a sample discharge operation of the sample insertion and recovery apparatus 2. When sample processing is started by the sample processing system 1, first, an operator operates the operation panel 21b of the sample insertion unit 21 to give a sample processing start instruction to the sample processing system 1. In this state, when a sample rack L is inserted into the sample insertion unit 21, the sample rack L placed in the rack placement section 211 is detected by the sensors 212 and 213 (Step S101). A control program which is executed by the control section 21a of the sample insertion unit 21 is an event-driven program, and the control section 21a of the sample insertion unit 21 executes the process of Step S102 when the sensors 212 and 213 detect the sample rack L.

In Step S102, the control section 21a drives the engagement sections 211a to move the sample rack L backward until the sample rack reaches the rack output position 214. Further, the control section drives the protrusion section 215 to output the sample rack L to the pre-processing unit 22 (Step S102).

The sample rack L output from the rack output position 214 of the rack insertion unit 21 is introduced into the pre-processing unit 22 in the leftward direction and reaches the barcode reading position. When the sample rack L reaches the barcode reading position, the control section 22a of the pre-processing unit 22 controls the barcode reading section 22b and reads a rack ID of the sample rack and sample IDs of sample containers T which are held in the sample rack L (Step S103). When the sample rack L reaches the barcode reading position, whether there is a sample container T is detected by the optical sensor of the barcode reading section 22b, and by the barcode reading section 22b, a sample barcode of each of the sample containers T is continuously read plural times.

When data of the sample IDs each of which is read plural times matches, the reading of the sample barcode is regarded as successful. In this manner, the sample IDs are read from the sample barcodes of all the sample containers T held in the sample rack L. The holding positions in the sample rack L are associated with the sample IDs read from the sample containers which are respectively held in the holding positions, and are stored in the control section 22a.

Next, the control section 22a controls the engagement sections 221a to transfer the sample rack L to the rack output position 222 on the rack placement section 221 (Step S104) and transmits the stored rack ID, holding positions and sample IDs to the system control apparatus 8 (Step S105). As will be described later, the system control apparatus 8 receiving the rack ID, holding positions and sample IDs inquires the examination information management apparatus 9 of measurement orders and stores the measurement orders in association with the rack ID, holding positions and sample IDs.

When the sample rack L reaches the rack output position 222, the control section 22a controls the barcode reader 222a to read the rack ID from the rack barcode of the sample rack L (Step S106) and transmits discharge instruction request data including the read rack ID to the system control apparatus 8 (Step S107). When receiving this discharge instruction request data, the system control apparatus 8 searches a measurement order corresponding to the same rack ID from the hard disk, decides a transport destination of the sample rack L on the basis of the search and transmits transport instruction data for transporting the sample rack L to the decided transport destination to the pre-processing unit 22. The control section 22a waits to receive the transport instruction data from the system control apparatus 8 (NO in Step S108). When receiving the transport instruction data (YES in Step S108), the control section controls the protrusion section 225 to output the sample rack L from the rack output position 222 in the leftward direction (Step S109) and ends the process.

Every time a new sample rack L is inserted into the sample insertion unit 21, the processes of the above-described Steps S101 to S109 are executed.

<Measurement Order Obtaining Operation of System Control Apparatus 8>

Figure 11:
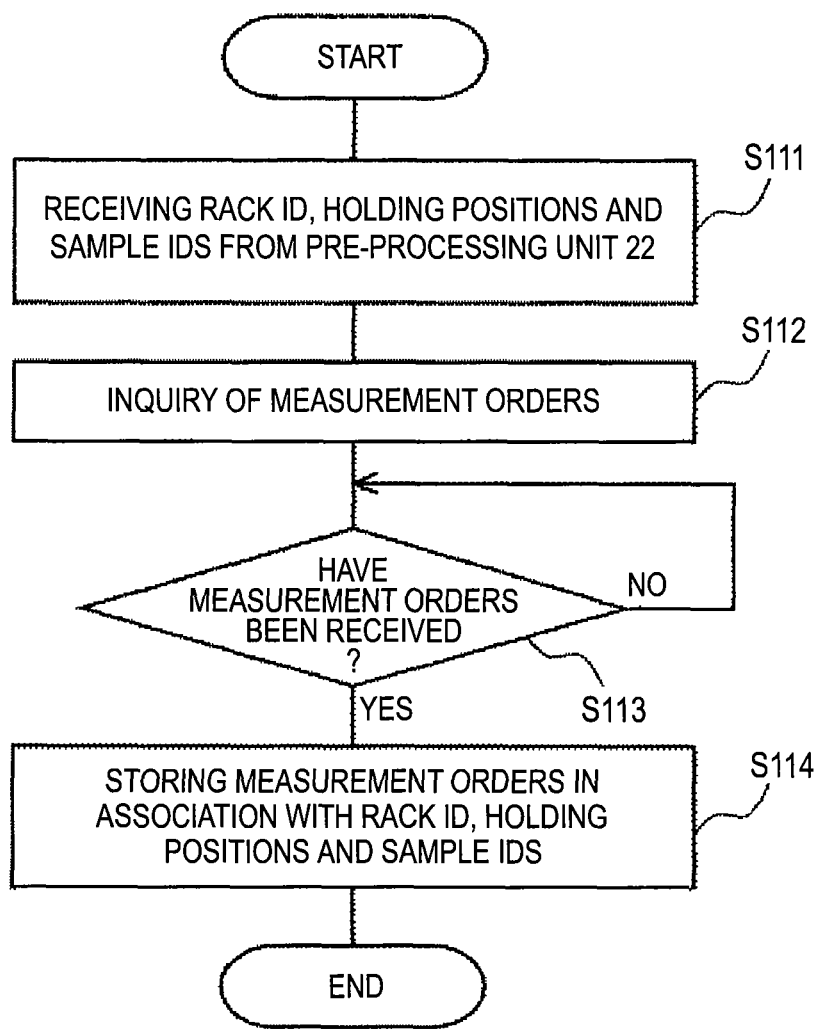
FIG. 11 is a flowchart showing the flow of a measurement order obtaining operation of the system control apparatus according to the first embodiment.

FIG. 11 is a flowchart showing the flow of a measurement order obtaining operation of the system control apparatus 8. The system control apparatus 8 receives the rack ID, holding positions and sample IDs transmitted from the pre-processing unit 22 via the communication interface 81g (Step S111). The system control program 84a is an event-driven program, and the CPU 81a executes the process of Step S112 when receiving the rack ID, holding positions and sample IDs.

In Step S112, for all of the received sample IDs, the CPU 81a inquires the examination information management apparatus 9 of measurement orders by transmitting measurement order request data including the sample IDs to the examination information management apparatus 9 (Step S112). Next, the CPU 81a waits to receive the measurement orders (NO in Step S113). When receiving the measurement orders (YES in Step S113), the CPU stores the measurement orders in the hard disk 81d in association with the rack ID, holding positions and sample IDs (Step S114) and ends the process.

<First Transport Instruction Operation of System Control Apparatus 8>

Figure 12:
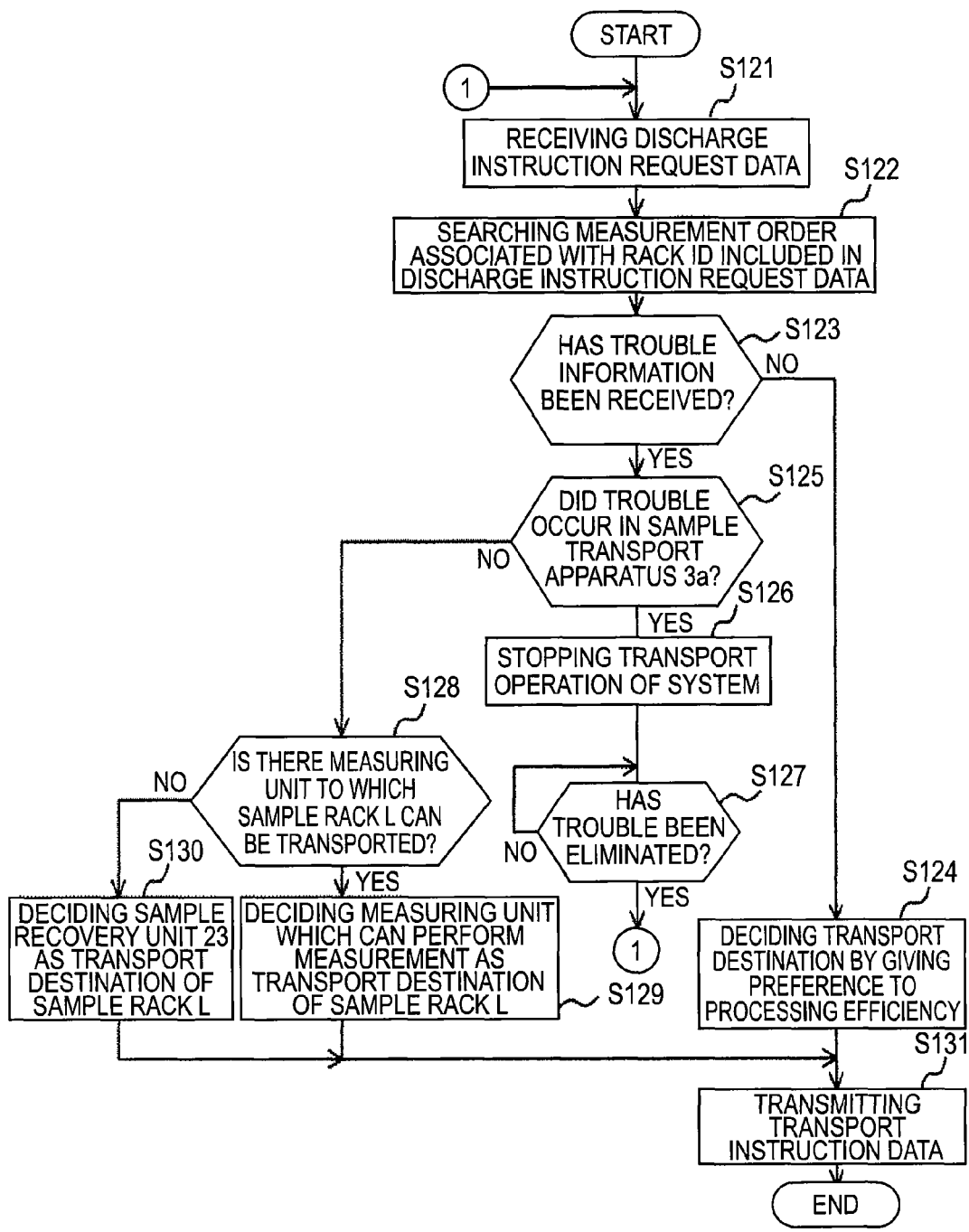
FIG. 12 is a flowchart showing the flow of a first transport instruction operation of the system control apparatus according to the first embodiment.

FIG. 12 is a flowchart showing the flow of a first transport instruction operation of the system control apparatus 8. When receiving the discharge instruction request data (rack ID) via the communication interface 81g (Step S121), the CPU 81a searches a measurement order associated with the received rack ID from the hard disk 81d (Step S122).

Next, the CPU 81a determines whether trouble information has been received (Step S123). The sample transport apparatuses 3a, 3b, 3c and 4 transmit trouble information including information (for example, trouble code) showing the kind of occurring trouble to the system control apparatus 8 when trouble such as breakdown occurs. When determining that the trouble information has not been received (NO in Step S123), the CPU 81a specifies the measuring unit 51, 52 or 53 which can most rapidly start sample processing and decides the specified unit as the transport destination of the sample rack L (Step S124).

The CPU 81a manages the transport status of the sample rack L in real time and can determine which one of the measuring units 51, 52 and 53 the sample is supplied to most rapidly start sample processing.

The CPU 81a manages the transport status of the sample rack L by inquiring the respective sample transport apparatuses 3a, 3b and 3c of whether the sample rack L is held in the pre-analysis rack holding section 33. For example, when the sample rack L is held in the pre-analysis rack holding section 33 of the sample transport apparatus 3a, the CPU 81a determines that the measuring unit 51 cannot receive the sample rack L. That is, in Step S124, the CPU 81a decides as the transport destination the measuring unit which can measure measurement items included in the measurement order of the sample held in the sample rack L and can receive the sample rack L.

When determining that the trouble information has been received (YES in Step S123), the CPU 81a determines whether the trouble occurred in the sample transport apparatus 3a on the basis of the trouble information (Step S125). When determining that the trouble occurred in the sample transport apparatus 3a (YES in Step S125), the CPU 81a stops the operation of transporting the sample rack L in the sample rack transport system 100 (Step S126) and waits for elimination of the trouble in the sample transport apparatus 3a (Step S127). When determining that the trouble in the sample transport apparatus 3a has been eliminated (YES in Step S127), the CPU 81a executes the process of Step S121.

When determining that the trouble did not occur in the sample transport apparatus 3a, that is, when determining that the trouble occurred in the sample transport apparatus 3b or 3c (NO in Step S125), the CPU 81a determines whether there is the transport unit which can transport the sample rack L (Step S128). Here, the CPU 81a determines whether the sample rack L can be transported to the measuring unit which can measure measurement items of the measurement order of the sample held in the sample rack L.

Hereinafter, a case in which the trouble occurs in the sample transport apparatus 3b will be described as a concrete example. When trouble occurs in the sample transport apparatus 3b, the sample rack L cannot be transported to the measuring units 52 and 53. Accordingly, when DIFF or RET is included in the measurement items of the measurement order of the sample held in the sample rack L, the CPU 81a determines that the sample rack L cannot be transported. On the other hand, when DIFF or RET is not included in the measurement items of the measurement order of the sample held in the sample rack L, the CPU 81a determines that the sample rack L can be transported to the measuring unit 51.

When determining that there is the transport unit which can transport the sample rack L (YES in Step S128), the CPU 81a decides as the transport destination the measuring unit which can perform measurement on the sample rack L (Step S129). According to the above-described concrete example, the CPU 81a decides the measuring unit 51 as the transport destination of the sample rack L. In addition, when determining that there is no transport unit which can transport the sample rack L (NO in Step S128), the CPU 81a decides the sample recovery unit 23 as the transport destination of the sample rack L (Step S130).

Next, the CPU 81a transmits transport instruction data showing an instruction for transporting the sample rack L to the transport destination to the sample insertion unit 2 and the sample transport apparatuses 3a, 3b and 3c (Step S130) and ends the process. This transport instruction data includes the rack ID of the sample rack L and the holding positions, sample IDs and measurement orders of all the samples which are held in the sample rack L. In the above-described concrete example, the CPU 81a transmits the transport instruction data to the sample transport apparatus 3a and the sample insertion and recovery apparatus 2.

<First Transport Operation of Sample Transport Apparatuses 3a, 3b and 3c>

Figure 13:
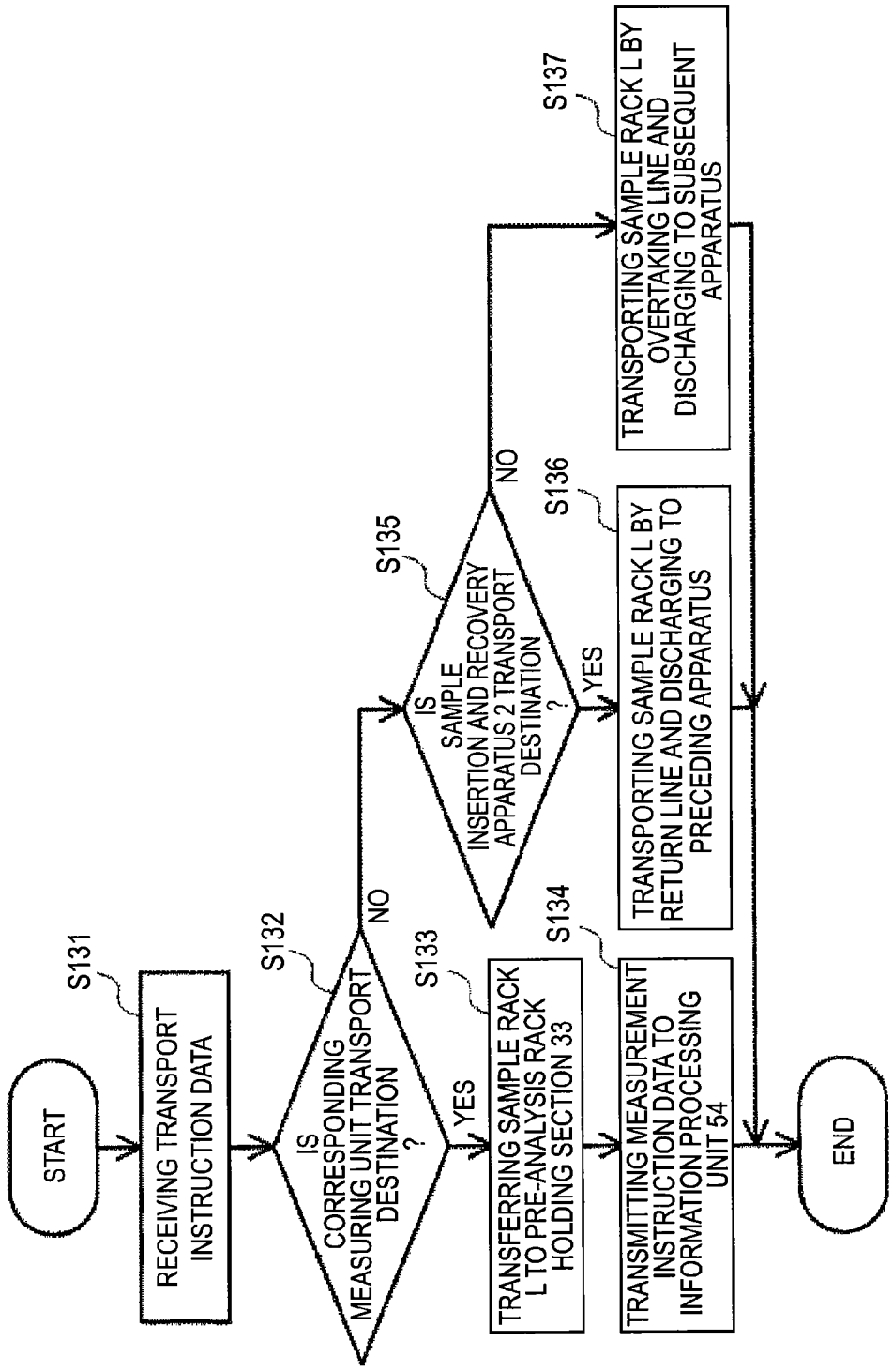
FIG. 13 is a flowchart showing the flow of a first transport operation of the sample transport apparatus for the blood cell analysis apparatus according to the first embodiment.

FIG. 13 is a flowchart showing the flow of a first transport operation of the sample transport apparatuses 3a, 3b and 3c. When the transport instruction data is received, the control section 22a of the pre-processing unit 22 moves the protrusion section 225 leftward to discharge the sample rack L at the rack output position 222 to the rack overtaking transport section 321 of the sample transport apparatus 3a. Meanwhile, when the transport instruction data is received (Step S131), the control section 32 of the sample transport apparatus 3 determines whether the transport destination of the sample rack L is the measuring unit corresponding to the sample transport apparatus on the basis of the received transport instruction data (Step S132). That is, the control section 32 of the sample transport apparatus 3a determines whether the transport destination of the sample rack L is the measuring unit 51, the control section 32 of the sample transport apparatus 3b determines whether the transport destination of the sample rack L is the measuring unit 52, and the control section 32 of the sample transport apparatus 3c determines whether the transport destination of the sample rack L is the measuring unit 53.

When determining that the transport destination is the corresponding measuring unit (YES in Step S132), the control section 32 controls the driving of the transport mechanism 31, introduces the sample rack L by the rack overtaking transport section 321 and moves the sample rack L positioned at the pre-analysis rack output position 323 to the pre-analysis rack holding section 33 by moving the rack output section 322 forward (Step S133). In addition, the control section 32 transmits the rack ID of the sample rack L and the holding positions, sample IDs and measurement instruction data including measurement orders of all the samples which are held in the sample rack L to the information processing unit 54 (step S134) and ends the process.

On the other hand, when determining that the transport destination is not the corresponding measuring unit (NO in Step S132) the control section 32 determines whether the transport destination of the sample rack L is the sample insertion and recovery apparatus 2, that is, whether the transport destination is the sample recovery unit 23 or 24 or not (Step S135). When determining that the transport destination is the sample insertion and recovery apparatus 2 (the sample recovery unit 23 or 24) (YES in Step S135), the control section 32 controls the driving of the transport mechanism 31, transfers the sample rack L to the rack return transport section 331 by the rack feeding mechanisms 34c, discharges the sample rack L to the preceding apparatus by the rack return transport section 331 (Step S136) and ends the process. When determining that the transport destination is not the sample insertion and recovery apparatus 2 (the sample recovery unit 23 or 24) (NO in Step S135), the control section 32 controls the driving of the transport mechanism 31, introduces the sample rack L by the rack overtaking transport section 321, directly discharges the sample rack L to the subsequent apparatus (Step S137) and ends the process.

Here, a transport operation by the sample transport apparatus 3a when the sample rack L for which the rack recovery unit 23 is the transport destination is discharged by the pre-processing unit 22 will be described.

When the sample rack L is not detected by the sensors 34a and 34b of the post-analysis rack holding section 34, the sample transport apparatus 3a transfers the sample rack L, which is discharged from the pre-processing unit 22, to the rack overtaking position 321a by the rack overtaking transport section 321, transfers the sample rack to the rack return position 331a by the rack feeding mechanisms 34c and discharges the sample rack to the sample insertion and recovery apparatus 2 by the rack return transport section 331.

On the other hand, when the sample rack L is detected by the sensors 34a and 34b of the post-analysis rack holding section 34, the operations of the sample transport apparatus 3a are different in accordance with which one of the detection of the sample rack L by the sensors 34a and 34b and the reading of the rack ID by the barcode reader 222a of the pre-processing unit 22 is more rapidly performed.

First, when the detection of the sample rack L by the sensors 34a and 34b is more rapidly performed, the pre-processing unit 22 waits for the transport of the sample rack L. Meanwhile, the sample transport apparatus 3a transfers the sample rack L in the post-analysis rack holding section 34 to the rack overtaking position 321a or the rack return position 331a by the rack feeding mechanisms 34c and transports the sample rack L by the rack overtaking transport section 321 or the rack return transport section 331. Then, the pre-processing unit 22 discharges the sample rack L, and the sample transport apparatus 3 transfers the discharged sample rack L to the rack overtaking position 321a by the rack overtaking transport section 321, transfers the sample rack to the rack return position 331a by the rack feeding mechanisms 34c and transports the sample rack to the sample insertion and recovery apparatus 2 by the rack return transport section 331.

Next, when the reading of the rack ID by the barcode reader 222a of the pre-processing unit 22 is more rapidly performed, the sample transport apparatus 3a causes the sample rack L transferred to the post-analysis rack holding section 34 to wait in the post-analysis rack holding section 34, transfers the sample rack L discharged from the sample insertion and recovery apparatus 2 to the rack overtaking position 321a by the rack overtaking transport section 321, transfers the sample rack to the rack return position 331a by the rack feeding mechanisms 34c, and transports the sample rack to the sample insertion and recovery apparatus 2 by the rack return transport section 331. Then, the sample transport apparatus 3a transfers the sample rack L in the post-analysis rack holding section 34 to the rack return position 331a by the rack feeding mechanisms 34c, transfers the sample rack to the rack overtaking position 321a or the rack return position 331a by the rack feeding mechanisms 34c and transports the sample rack L by the rack overtaking transport section 321 or the rack return transport section 331.

Figure 14:
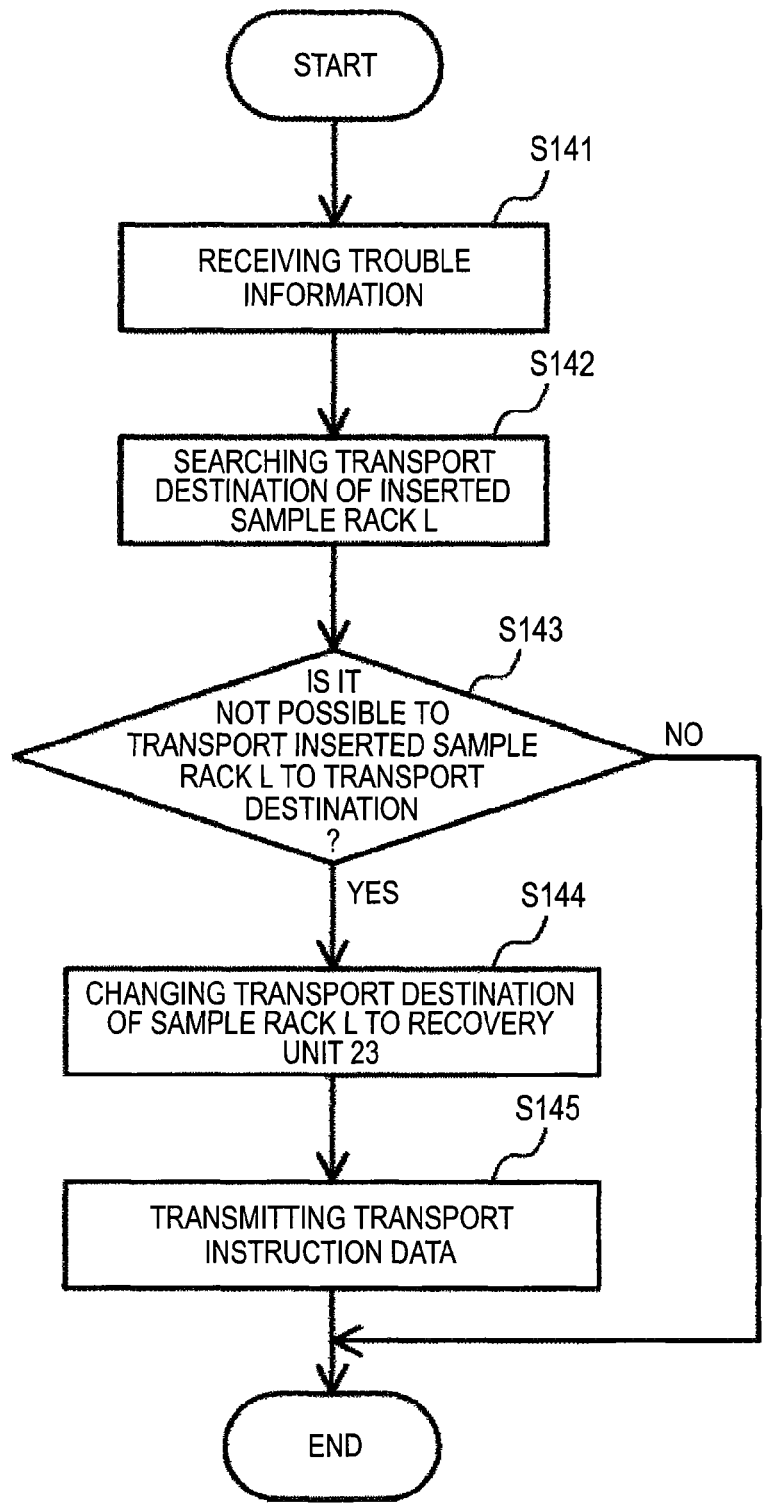
FIG. 14 is a flowchart showing the flow of a transport destination change process when trouble occurs in the system control apparatus according to the first embodiment.

FIG. 14 is a flowchart showing the flow of a transport destination chance process of the system control apparatus 8. This process is a process for changing the transport destination of the sample rack L which is inserted into the sample transport apparatus when trouble occurs.

In the hard disk 81d of the system control apparatus 8, the transport destination of the sample rack L which is inserted into the sample transport apparatus is stored. When receiving trouble information from the sample transport apparatus (Step S141), the CPU 81a searches the transport destination of the sample rack L from the hard disk 81d (S142). Next, on the basis of the search result in Step S142, the CPU 81a determines whether the inserted sample rack L can be transported to the transport destination when trouble occurs (Step S143).

For example, when trouble occurs in the sample transport apparatus 3b, the sample rack L can be transported to the measuring unit 51, but cannot be transported to the measuring units 52 and 53.

Accordingly, when trouble occurs in the sample transport apparatus 3b, the CPU 81a determines that the sample rack L can be transported to the transport destination when the transport destination of the sample rack L is the measuring unit 51. When the transport destination of the sample rack L is the measuring unit 52 or 53, the CPU 81a determines that the sample rack L cannot be transported to the transport destination.

When determining that the sample rack L cannot be transported to the transport destination (YES in Step S143), the CPU 81a changes the transport destination of the sample rack L to the sample recovery unit 23 (Step S144), transmits transport instruction data to the sample insertion and recovery apparatus 2 and the sample transport apparatuses 3a, 3b and 3c (Step S145) and ends the process. In addition, the CPU 81a ends the process also when determining that the sample rack L can be transported to the transport destination (NO in Step S143).

<Rack Transport Control Operation of Blood Cell Analysis Apparatus 5>

Figure 15:
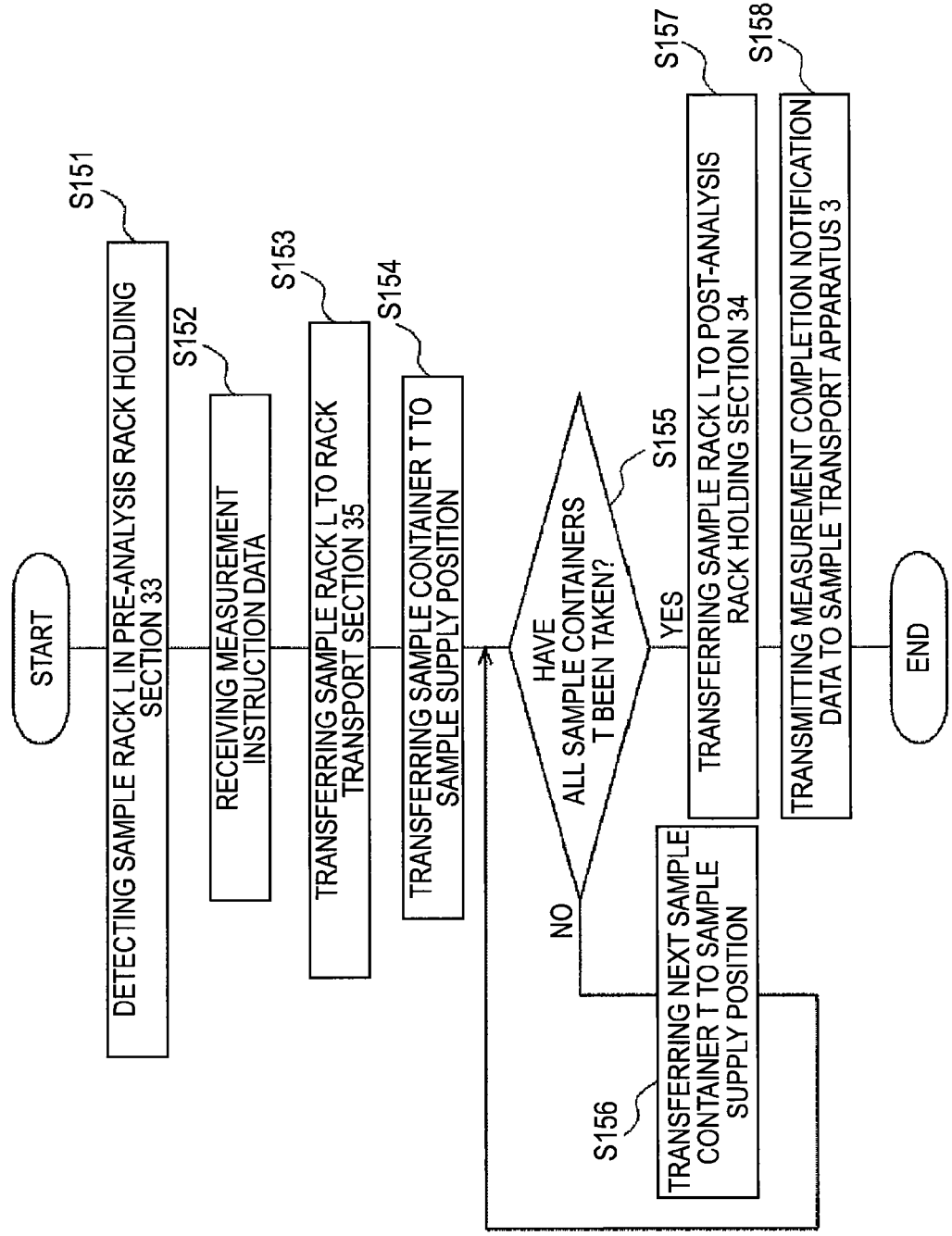
FIG. 15 is a flowchart showing the flow of a rack transport control operation of the blood cell analysis apparatus according to the first embodiment.

FIG. 15 is a flowchart showing the flow of a rack transport control operation of the blood cell analysis apparatus 5. The CPU 541a of the information processing unit 54 of the blood cell analysis apparatus 5 detects the sample rack L in the pre-analysis rack holding section 33 by the rack sensors provided in the sample transport apparatus 3a, 3b and 3c (Step S151). When receiving measurement instruction data from the sample transport apparatus 3a, 3b and 3c (Step S152), the CPU executes the process of Step S153.

In Step S153, the CPU 541a moves the rack feeding sections 33b backward to transfer the sample rack L to the rack transport section 35. Next, the CPU 541a controls the driving of the rack transport section 35 and transports the sample rack L so as to position the sample container T at the sample supply position (Step S154).

In a sample analysis operation to be described later, the sample container T which is positioned at the sample supply position is removed from the sample rack L and taken into the measuring unit. The sample is suctioned from the sample container T and is analyzed. When the suction of the sample in the measuring unit is completed, the sample container T is returned to the sample rack L. In addition, the CPU 541a determines whether all the sample containers T in the sample rack L have been taken (Step S155). When determining that all the sample containers T in the sample rack L have not been taken (NO in Step S155), that is, when there is a sample container T which has not been taken, the CPU 541a controls the driving of the rack transport section 35 to transport the sample rack L so that the holding position at which the next sample container T is detected is positioned at the sample supply position (Step S156) and returns the process to Step S155.

In Step S155, when determining that all the sample containers T which are held in the sample rack L have been taken (YES in Step S155), the CPU 541a controls the driving of the rack transport section 35 to transport the sample rack L up to the post-analysis rack output position 391 and further controls the driving of the rack output section 39 to transfer the sample rack L to the post-analysis rack holding section 34 (Step S157), transmits measurement completion notification data including the rack ID of the sample rack L to the corresponding sample transport apparatus (Step S158) and ends the process.

<Sample Analysis Operation of Blood Cell Analysis Apparatus 5>

Figure 16:
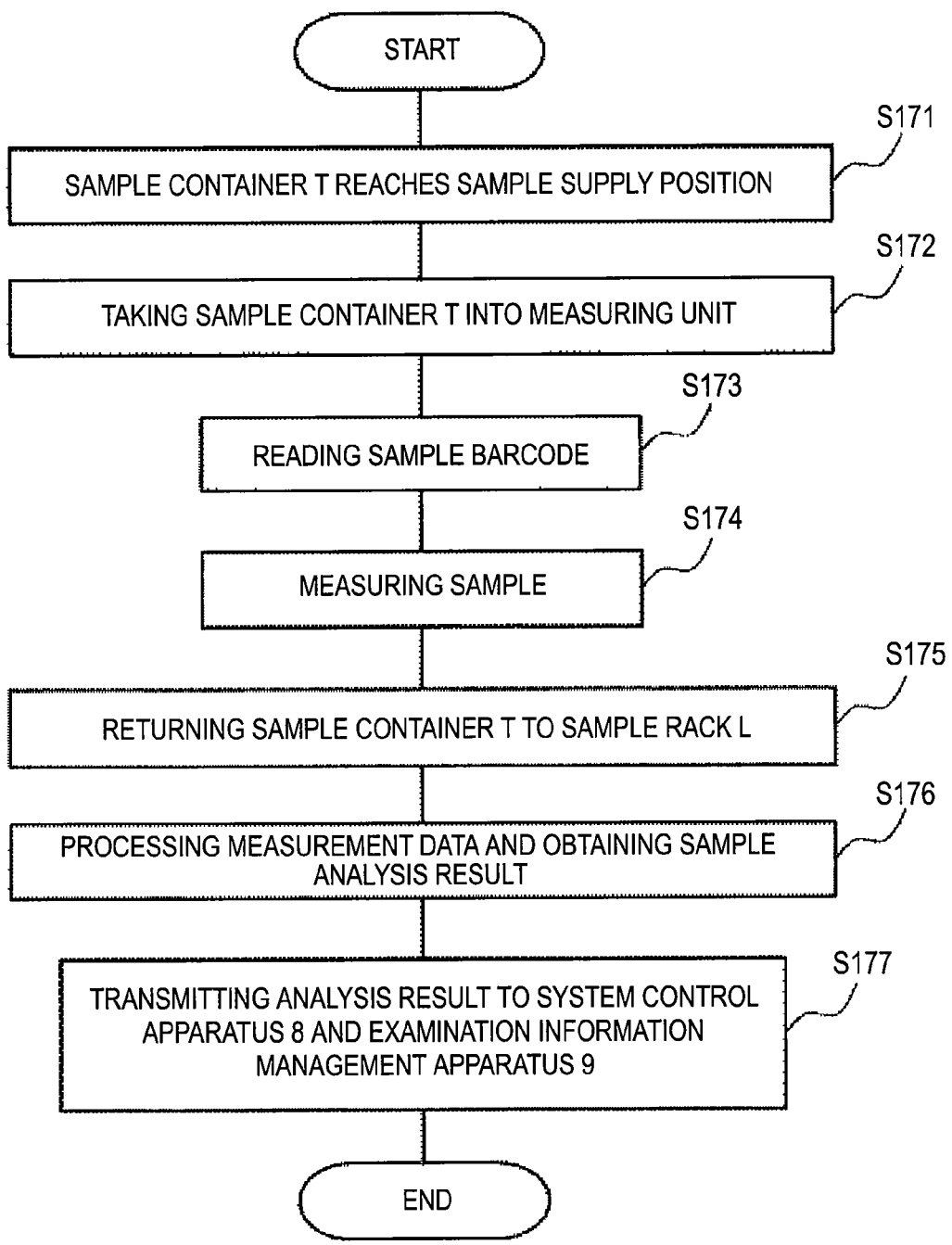
FIG. 16 is a flowchart showing the flow of a sample analysis operation of the blood cell analysis apparatus according to the first embodiment.

FIG. 16 is a flowchart showing the flow of a sample analysis operation of the blood cell analysis apparatus 5. The above-described rack transport control operation of the blood cell analysis apparatus 5 and the present sample analysis operation are executed in parallel by a multitasking process. The CPU 541a executes the process of Step S172 when the sample container T which is held in the sample rack L reaches the sample supply position (Step S171).

In Step S172, the CPU 541a removes the sample container T positioned at the sample supply position from the sample rack L and takes the sample container into the measuring unit by controlling the sample container transport section 515 of the measuring unit (Step S172). Further, the CPU 541a oscillates the sample container T by controlling the hand section 515a to stir the sample therein, and then controls the sample container transport section 515 to transport the sample container T to the barcode reading position 516 and reads the sample barcode of the sample container T by the barcode reading section 516, thereby obtaining the sample ID (Step S173).

Then, the CPU 541a measures the sample by using a measurement order included in the measurement instruction data (step S174).

The CPU 541a suctions the sample in an amount necessary for measurement from the sample container T, prepares a measurement specimen, starts the measurement of the sample, and then controls the sample container transport section 515 of the measuring unit to return the sample container T to the sample rack L from the measuring unit (Step S175). Then, in the above-described rack transport control operation, the rack transport section 35 is controlled and the sample rack L is thus transported in the X1 direction. The CPU 541a processes measurement data which is obtained by measuring the sample and obtains a sample analysis result (Step S176). Next, the CPU 541a transmits the obtained analysis result to the system control apparatus 8 and the examination information management apparatus 9 (Step S177) and ends the process.

<Second Transport Instruction Operation of System Control Apparatus 8>

Figure 17:
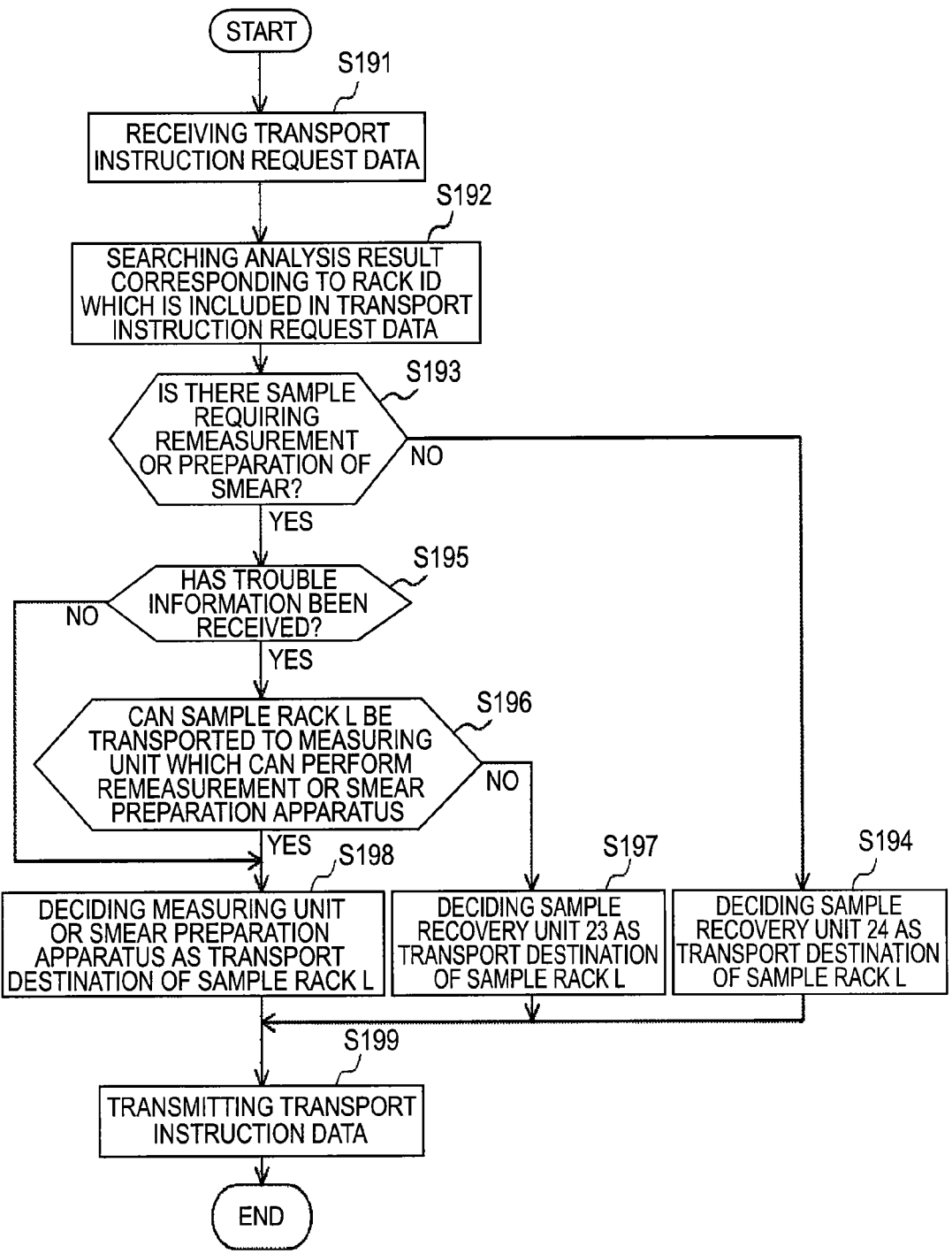
FIG. 17 is a flowchart showing the flow of a second transport instruction operation of the system control apparatus according to the first embodiment.

FIG. 17 is a flowchart showing the flow of a second transport instruction operation of the system control apparatus 8. As will be described later, the sample rack L, in which the samples were measured and which was transferred to the post-analysis rack holding section 34 from the post-analysis rack output position 391, is detected by the sensors 34a and 34b. In addition, the measurement completion notification data transmitted from the information processing unit 54 is received by the corresponding sample transport apparatus. At this time, the sample transport apparatus transmits transport instruction request data including the rack ID of the sample rack L to the system control apparatus 8. When receiving the transport instruction request data (Step S191), the CPU 81a of the system control apparatus 8 searches the analysis result corresponding to the rack ID which is included in the transport instruction request data from the hard disk 81d (Step S192).

The CPU 81a determines whether a sample requiring remeasurement or a microscopic test is included in the samples held in the sample rack L (Step S193). When determining that a sample requiring remeasurement or a microscopic test is not included (NO in Step S193), the CPU 81a decides the sample recovery unit 24 as the transport destination of the sample rack L (Step S194). When determining that a sample requiring remeasurement or a microscopic test is included (YES in Step S193), the CPU 81a determines whether trouble information is received (Step S195). When determining that the trouble information is not received (NO in Step S195), the CPU 81a advances the process to Step S198.

When determining that the trouble information is received (YES in Step S195), the CPU 81a determines whether the sample rack can be transported to the smear preparation apparatus 6 or the measuring unit capable of performing remeasurement of the sample in the sample rack L (Step S196). In greater detail, when trouble occurs in the sample transport apparatus 3b, measurement is performed in the sample rack L by the measuring unit 51 and a sample requiring remeasurement by the measuring unit 52 or 53 is included, the CPU 81a determines that the sample rack L cannot be transported to any measuring unit.

When determining that the sample rack L cannot be transported to the smear preparation apparatus 6 or the measuring unit capable of performing remeasurement (NO in Step S196), the CPU 81a decides the sample recovery unit 23 as the transport destination of the sample rack L (Step S197). When determining that the sample rack L can be transported to the smear preparation apparatus 6 or the measuring unit capable of performing remeasurement (YES in Step S196), the CPU 81a decides the smear preparation apparatus 6 or the measuring unit as the transport destination (Step S198).

After decision of the transport destination of the sample rack L as described above, the CPU 81a transmits transport instruction data showing an instruction for transporting the sample rack L to the decided transport destination to the sample insertion and recovery apparatus 2 and the sample transport apparatuses 3a, 3b and 3c (Step S199) and ends the process.

<Second Transport Operation of Sample Transport Apparatuses 3a, 3b and 3c>

Figure 18:
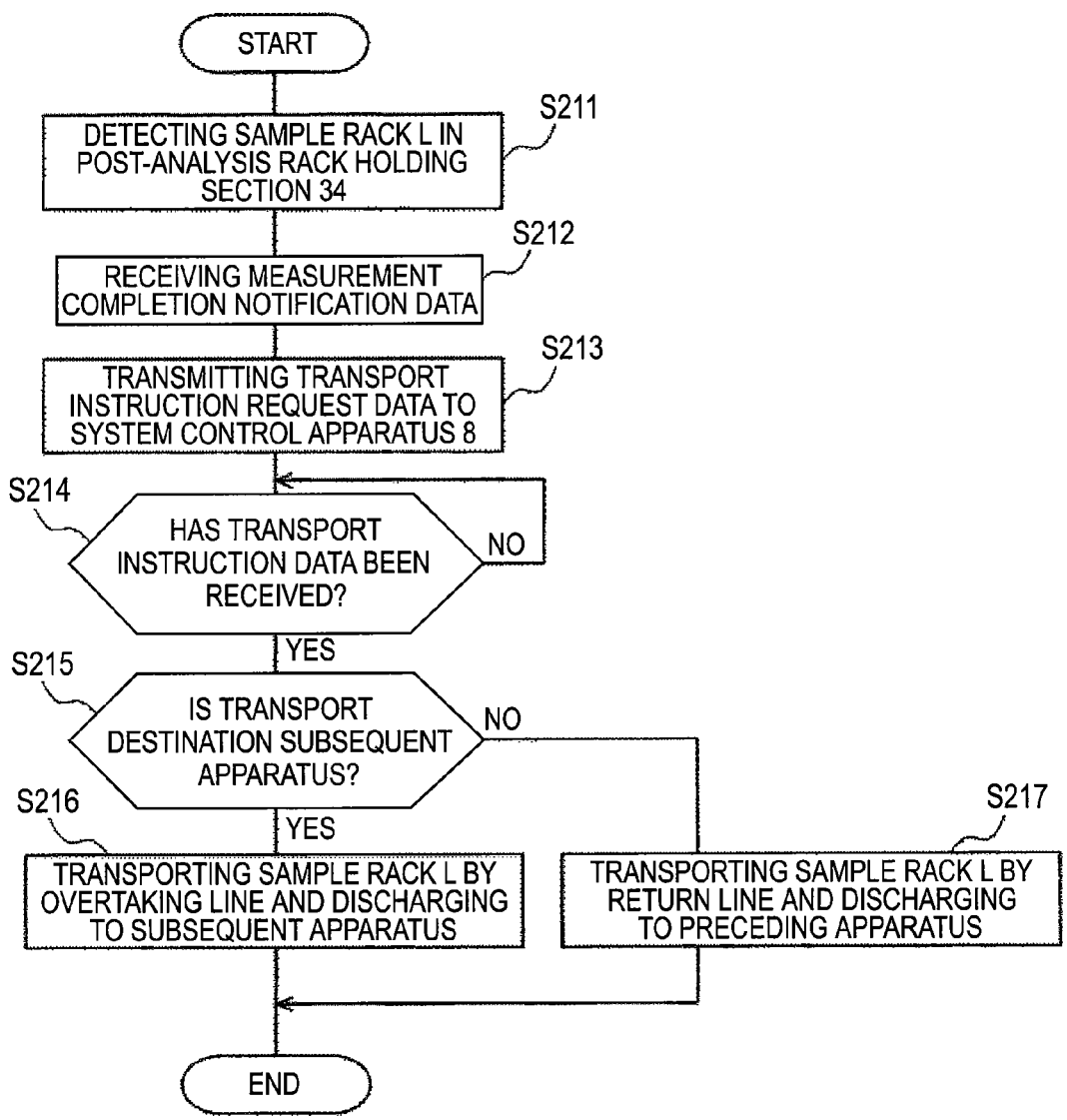
FIG. 18 is a flowchart showing the flow of a second transport operation of the sample transport apparatus according to the first embodiment.

FIG. 18 is a flowchart showing the flow of a second transport operation of the sample transport apparatuses 3a, 3b and 3c. As described above, when the sample rack L is transferred to the post-analysis rack holding section 34 by the rack output section 39, the sample rack L is detected by the rack sensor (Step S211). In addition, when the sample rack L is transferred to the post-analysis rack holding section 34 by the rack output section 39, the measurement completion notification data which is transmitted from the information processing unit 54 is received (Step S212). The control section 32 detects the sample rack L in the post-analysis rack holding section 34 by the rack sensors. When receiving the measurement completion notification data from the information processing unit 54, the control section executes the process of Step S213.

In Step S213, the control section 32 transmits transport instruction request data including the rack ID of the sample rack L to the system control apparatus 8 (Step S213). As described above, when receiving the transport instruction request data, the system control apparatus 8 decides the transport destination of the sample rack L and transmits transport instruction data for transporting the sample rack L to the transport destination to the sample transport apparatuses 3a, 3b and 3c. The control section 32 waits to receive the transport instruction data (NO in Step S214). When receiving the transport instruction data (YES in Step S214), the control section determines whether the transport destination which is shown in the transport instruction data is the subsequent measuring unit or the smear preparation apparatus 6 or not (Step S215). When the transport destination which is shown in the transport instruction data is the subsequent measuring unit or the smear preparation apparatus 6 (YES in Step S215), the control section 32 controls the driving of the transport mechanism 31, transfers the sample rack L to the rack overtaking transport section 321 by the rack feeding sections 33b, and then discharges the sample rack L to the transport direction downstream side by the rack overtaking transport section 321 (Step S216) and ends the process.

In addition, when determining that the transport destination which is shown in the transport instruction data is not the subsequent measuring unit or the smear preparation apparatus 6, that is, when determining that the transport destination is the sample recovery unit 23 or 24 (NO in Step S215), the control section 32 controls the driving of the transport mechanism 31, transfers the sample rack L to the rack return transport section 331 by the rack feeding sections 33b, discharges the sample rack L to the preceding apparatus by the rack return transport section 331 (Step S217) and ends the process.

When the sample rack L is discharged to the apparatus on the transport direction upstream side from the rack return transport section 331 of the sample transport apparatus 3b, 3c or 4, the apparatus introducing the sample rack L transports the sample rack L to the transport direction upstream side by the rack return transport section 331 and discharges the sample rack L to the apparatus on the upstream side.

<Rack Sorting and Recovery Operation of Sample Insertion and Recovery Apparatus 2>

Figure 19:
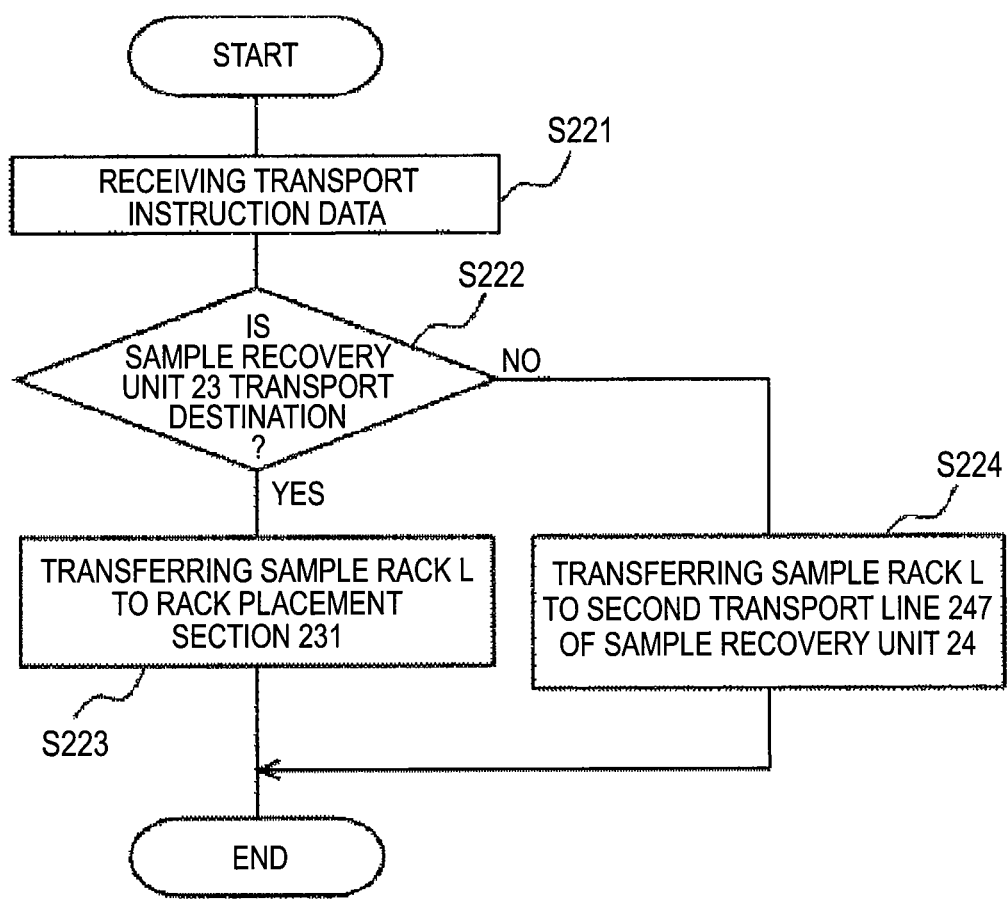
FIG. 19 is a flowchart showing the flow of a rack sorting and recovery operation of the sample insertion and recovery apparatus according to the first embodiment.

FIG. 19 is a flowchart showing the flow of a rack sorting and recovery operation of the sample insertion and recovery apparatus 2. This rack sorting and recovery operation is an operation which is executed by the respective control sections of the sample insertion unit 21 and the sample recovery units 23 and 24 and is started by receiving the above-described transport instruction data from the system control apparatus 8 in Step S221. Hereinafter, the rack sorting and recovery operation will be described which is executed by the control section 23a of the sample recovery unit 23.

When receiving the above-described transport instruction data from the system control apparatus 8 (Step S221), the control section 23a of the sample recovery unit 23 determines whether the transport destination of the sample rack L which is introduced into the second transport line 237 via the return line, the transport line 223 of the pre-processing unit 22 and the second transport line 217 is the sample recovery unit 23 on the basis of the transport instruction data (Step S222). When determining that the transport destination is the sample recovery unit 23 (YES in Step S222), the control section 23a transfers the sample rack L introduced into the second transport line 237 to the rack placement section 231 by driving the rack transfer section 238 (Step S223) and ends the process. In this manner, the sample rack L is recovered by the sample recovery unit 23.

When determining that the transport destination is not the sample recovery unit 23 (NO in Step S222), the control section 23a transports the sample rack L to the transport direction upstream side (X2 direction) by driving the second transport line 237 and discharges the sample rack L to the second transport line 247 toward the sample recovery unit 24 (Step S224).

As described above, in the sample rack transport system 100 according to this embodiment, even when trouble occurs in one of the plurality of sample transport apparatuses 3b, 3c and 4, excluding the sample transport apparatus 3a on the most upstream side, the sample rack transport operation is not stopped in the entire system. Therefore, according to the sample rack transport system 100 according to this embodiment, sample measurement efficiency can be improved even when trouble occurs.

When trouble is eliminated, a user is required to manually insert the sample rack L, in which necessary measurement has not yet been completed, into the sample insertion unit 21. Here, in the sample rack transport system 100 according to this embodiment, the sample rack L is recovered by the sample recovery unit 23 adjacent to the sample insertion unit 21. Accordingly, in the sample rack transport system 100 according to this embodiment, it is easy for the user to reinsert the sample rack L.

(Second Embodiment)

This embodiment is almost the same as the first embodiment. However, the configuration of a sample insertion and recovery apparatus 2 and the recovery destination of a sample rack L are different.

Figure 20:
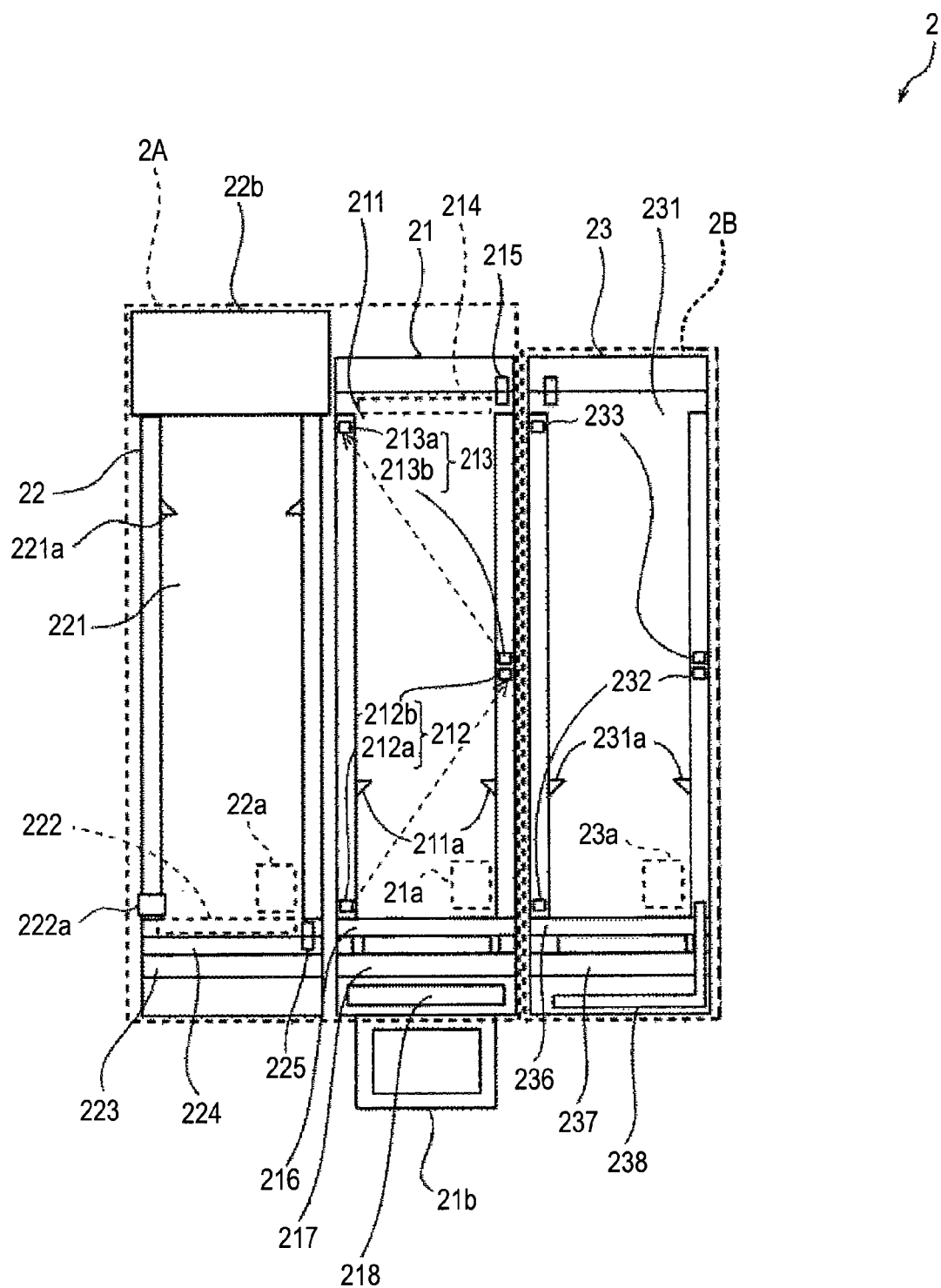
FIG. 20 is a plan view showing the configuration of a sample insertion and recovery apparatus according to a second embodiment.

FIG. 20 is a plan view of the sample insertion and recovery apparatus 2 according to this embodiment. As shown in FIG. 20, the sample insertion and recovery apparatus 2 according to this embodiment includes a sample insertion unit 21, a pre-processing unit 22 and a recovery unit 23. In this embodiment, a sample rack L in which necessary measurement has not yet been completed is transported to the sample insertion unit 21 and a sample rack L in which necessary measurement has been completed is transported to the recovery unit 23.

When trouble is eliminated, a system control apparatus 8 transmits a transport instruction to the sample insertion and recovery apparatus 2. Since the subsequent processes are the same as the processes of Steps S103 to S109 in the sample discharge operation of the sample insertion and recovery apparatus 2 in the first embodiment 1, the description thereof will be omitted.

In a sample rack transport system 100 according to this embodiment, a sample rack L in which necessary measurement has not yet been completed can be automatically reinserted to the sample rack transport system 100. Accordingly, it is possible to save the effort of reinsertion of the sample rack L into the sample rack transport system 100 by a user.

(Other Embodiments)

In the above-described embodiments, the computer 8a of the system control apparatus 8 decides the recovery destination of a sample rack L and the control section of the sample recovery unit controls the operations of the rack transfer section and the second transport line on the basis of the decided recovery destination, and therefore, the sorting and recovery of the sample rack L is performed. However, the invention is not limited thereto. The sorting and recovery of the sample rack L may be performed by executing the process of deciding the recovery destination of the sample rack L and the process of controlling the operations of the rack transfer section and the second transport line with a single computer (control section).

In the above-described embodiments, the configuration has been described in which the sample processing system 1 includes the blood cell analysis apparatus 5 which classifies blood cells included in a sample and counts the number of blood cells for each blood cell kind, but the invention is not limited thereto. The sample processing system may include a sample analysis apparatus other than the blood cell analysis apparatus, such as an immunological analysis apparatus, a blood coagulation measurement apparatus, a biochemical analysis apparatus and a urine analysis apparatus, and transport a blood sample or an urine sample to a measuring unit of the sample analysis apparatus.

In the above-described embodiments, the configuration has been described in which the blood cell analysis apparatus 5 includes the three measuring units 51, 52 and 53 and the information processing unit 54, but the invention is not limited thereto. One or plural measuring units may be provided, and the measuring unit and the information processing unit may be formed integrally with each other. In addition, a configuration may be provided in which the mechanisms in the measuring units 51, 52 and 53 are not controlled by the information processing unit 54, but each of the measuring units has a control section formed of a CPU, a memory and the like so as to control the measuring units by the control sections, measurement data which is obtained by the respective measuring units is processed by the information processing unit and thus a sample analysis result is generated.

In the above-described embodiments, the configuration has been described in which all the processes of the computer program 84a are executed by the single computer 8a, but the invention is not limited thereto. A distribution system may be provided which distributes the same processes as the above-described computer program 84a to plural devices (computers) and executes the processes.

In the above-described embodiments, as a concrete example, the case has been described in which trouble occurs in the sample transport apparatus 3b. However, of course, the sample rack transport system 100 according to the above-described embodiment executes the same process even when trouble occurs in the sample transport apparatus 3c.

In a case in which trouble occurs in the sample transport apparatus 3c when the sample recovery unit 23 is decided as the transport destination of a sample rack L in the first transport instruction of the system control apparatus 8, the sample rack L may be discharged to the sample transport apparatus 3a from the pre-processing unit 22 and the sample transport apparatus 3a may transfer the sample rack L output from the sample insertion and recovery apparatus 2 to the rack overtaking position 321a, transfer the sample rack to the rack return position 331a by the rack feeding mechanisms 34c and discharge the sample rack to the sample insertion and recovery apparatus 2 by the rack transport section 35.

In the above-described embodiments, when DIFF is included in measurement items of the measurement order of a sample held in a sample rack L and trouble occurs in the sample transport apparatus 3b, the sample recovery unit 23 is decided as the transport destination. However, the invention is not limited thereto. For example, when CBC and DIFF are included in measurement items of the measurement order of a sample held in a sample rack L, the measuring unit 51 may be decided as the transport destination of the sample rack L. In this case, only CBC may be measured in the measuring unit 51 and then the sample recovery unit 23 may be decided as the transport destination of the sample rack L by the system control apparatus 8. In this manner, the measurement items which can be measured in the measuring unit are measured and thus sample processing efficiency can be improved. The same is also applied to a case in which trouble occurs in the sample transport apparatus 3c when RET and CBC or DIFF are included in measurement items of the measurement order of a sample held in a sample rack L.

The trouble in the above-described embodiments is a severe problem which requires repair by a service man, but the invention is not limited thereto. The trouble may be a small problem such as a mistake in the transport of a sample rack.

In the above-described embodiments, the sample transport apparatuses 3a, 3b and 3c includes the rack overtaking transport section 321 which transports a sample rack L by driving the transport belt in the transport downstream direction with a stepping motor and the rack return transport section 331 which transports a sample rack L by driving the transport belt in the transport upstream direction with the stepping motor. However, the invention is not limited thereto. For example, a configuration may be provided in which the sample transport apparatuses 3a, 3b, 3c and 4 have a transport belt and a stepping motor driving the transport belt to transport a sample rack by a single transport section which can switch the driving direction of the transport belt into the transport downstream direction and the transport upstream direction. In this case, a sample rack L which is determined that there is a measuring unit to which the sample rack can be transported by the system control apparatus 8 is discharged to the sample transport apparatus 3a by the pre-processing unit 22, is transported to the pre-analysis rack output position 323 by the transport belt which is driven in the transport downstream direction, and is fed to the pre-analysis rack holding section 33 by the rack feeding sections 33b. When the measurement is completed, the sample rack L is fed to the rack overtaking position 321a from the post-analysis rack holding section 34 by the rack feeding mechanisms 34c and is transported to the rack recovery unit 24 by the transport belt which is driven in the transport upstream direction. On the other hand, a sample rack L which is determined that there is no measuring unit to which the sample rack can be transported by the system control apparatus 8 is discharged to the sample transport apparatus 3a by the pre-processing unit 22 first, and is transported to the rack recovery section 23 by the transport belt which is driven in the transport upstream direction. Here, the sample rack L which is determined that there is no measuring unit to which the sample rack can be transported by the system control apparatus 8 may be directly transported to the rack recovery section 23 from the pre-processing unit 22.

In the above-described embodiments, each of the sample transport apparatuses 3a, 3b and 3c includes both of the rack overtaking transport section 321 transporting a rack to the downstream and the rack return transport section 331 transporting a rack to the upstream. However, the invention is not limited thereto. For example, each of the sample transport apparatuses 3a, 3b and 3c may include a unit which has a mechanism transporting a rack to the upstream and a unit which has a mechanism transporting a rack to the downstream. That is, a configuration may be provided in which each of the sample transport apparatuses 3a, 3b and 3c includes a first sample transport unit having at least the rack overtaking transport section 321 and a second sample transport unit having at least the rack return transport section 331.

In the above-described embodiments, when determining that the inserted sample rack L cannot be transported to the transport destination in Step S143, the CPU 81a changes the transport destination of the sample rack L to the sample recovery unit 23, but the invention is not limited thereto. In the invention, the CPU 81a may change the transport destination of the inserted sample rack L to another measuring unit which can perform measurement on the sample rack L. For example, when the measuring unit 53 is decided as the transport destination before the insertion of the sample rack L into the sample transport apparatus and trouble occurs in the sample transport apparatus 3c corresponding to the measuring unit 53 after insertion of the sample rack L, the CPU 81a may change the transport destination of the sample rack L, for which the measuring unit 53 is decided as the transport destination, to either of the measuring units 51 and 52 which can measure the sample in the sample rack L.

What is claimed is:

1. A sample processing apparatus comprising:
   a plurality of testing units arranged along a transport path and each operable to perform at least one type of test, wherein at least one of the plurality of testing units is operable to perform one type of test that is not performable by a remainder of the plurality of test units;
   a plurality of transport units configured to collectively form the transport path and collectively function to transport a target sample, which requires a certain type of test to be performed thereon, to a selected one of the plurality of testing units which is operable to perform the required type of test on the target sample;
   a sample collecting unit for placing a sample rack; and
   at least one processor of a computer system and at least one memory that stores programs for programming the at least one processor to determine whether a trouble of any transport unit is reported, wherein the at least one processor is further programmed to perform, when the at least one processor determines that a trouble of a transport unit is reported, the following operations, which are to:
      determine whether there are any testing units reachable by the target sample, wherein the troubled transport unit causes at least some of the plurality of testing units to be unreachable by the target sample;
      upon a determination by the at least one processor that there is a testing unit found reachable by the target sample, determine whether the reachable testing unit is operable to perform the required type of test on the target sample, based on types of test performable by the reachable testing unit;
      upon a determination by the at least one processor that the reachable testing unit is operable to perform the required type of test on the target sample, instruct to transport the target sample to the reachable testing unit; and
      upon a determination by the at least one processor that the reachable testing unit is not operable to perform the required type of test on the target sample, instruct to transport the target sample to the sample collecting unit.

2. The sample processing apparatus according to claim 1, further comprising a sample feeding unit that is located upstream of the plurality of transport units and places samples on the transport path for delivery, wherein the samples are placed in the sample feeding unit and waiting to be delivered for initial testing.

3. The sample processing apparatus according to claim 1, wherein the target sample is located at the selected one of the testing units and waiting for re-testing.

4. The sample processing apparatus according to claim 1, wherein the transport path is linear, and the at least one processor is programmed to determine that each testing unit located downstream of the troubled transport unit is unreachable for testing.

5. The sample processing apparatus according to claim 1, wherein, the at least one processor is programmed to instruct to transport the target sample to the sample collecting unit if none of the testing units is reachable by the target sample.

6. The sample processing apparatus according to claim 5, wherein the sample collecting unit includes first and second collecting sections that collect samples back from the transport path, and the at least one processor is programmed to instruct to transport the target sample to the first collecting section if the required type of test has been performed on the target sample or to the second collecting section if the required type of test remains to be performed on the target sample.

7. The sample processing apparatus according to claim 1, further comprising a sample feeding unit that places samples on the transport path for delivery to the selected one of the plurality of the testing units, wherein if there are no testing units reachable by the target sample, and a sample is not transportable to the sample collecting unit, the at least one processor is programmed to instruct to halt operation of the sample feeding unit.

8. The sample processing apparatus according to claim 1, further comprising a sample feeding unit that places samples on the transport path for delivery to the selected one of the plurality of the testing units, wherein the sample collecting unit is disposed near the sample feeding unit.

9. The sample processing apparatus according to claim 8, wherein the sample collecting unit is disposed on an upstream side of the sample feeding unit.

10. The sample processing apparatus according to claim 9, wherein each transport unit comprises a transport path that includes a first transport path for transporting a sample without passing through a testing unit and a second transport path for transporting a sample in a direction opposite to that of the first transport path,
the sample feeding unit places samples on the first transport path, and
the sample collecting unit collects samples from the second transport path.

11. The sample processing apparatus according to claim 9, wherein the sample feeding unit is configured to collect samples transported back from the transport path, and
the at least one processor is programmed to instruct to transport the target sample to the sample collecting unit if the required type of test has been performed on the target sample, or to transport the target sample to the sample feeding unit if the required type of test remains to be performed on the target sample, wherein the target sample collected by the sample feeding unit is placed on the transport path from the sample feeding unit for delivery to the selected one of the plurality of the testing units.

12. The sample processing apparatus according to claim 1, wherein the at least one processor is programmed to find the required type of test to be performed on the target sample and determine the selected one of the plurality of testing units to which the target sample is to be transported.

13. The sample processing apparatus according to claim 1, wherein when the at least one processor determines, after the target sample is placed on the transport path, that a trouble of a transport unit is reported, and the at least one processor further determines that the selected one of the plurality of the testing units is not reachable by the target sample because of the troubled transport unit, the at least one processor is programmed to change a transport destination of the target sample to the sample collecting unit.

* * * * *